United States Patent
Lee

(10) Patent No.: US 10,182,635 B2
(45) Date of Patent: Jan. 22, 2019

(54) INSTANT COSMETIC PREPARATION DEVICE AND THROWAWAY MIXING CONTAINER THEREFOR

(71) Applicant: AEVE CO. LTD., Seoul (KR)

(72) Inventor: Chi Hun Lee, Bucheon-si (KR)

(73) Assignee: AEVE CO. LTD., Seoul (KR)

( * ) Notice: Subject to any disclaimer, the term of this patent is extended or adjusted under 35 U.S.C. 154(b) by 560 days.

(21) Appl. No.: 14/773,386

(22) PCT Filed: Mar. 11, 2014

(86) PCT No.: PCT/KR2014/002016
§ 371 (c)(1),
(2) Date: Oct. 26, 2015

(87) PCT Pub. No.: WO2014/142527
PCT Pub. Date: Sep. 18, 2014

(65) Prior Publication Data
US 2016/0051029 A1    Feb. 25, 2016

(30) Foreign Application Priority Data

Mar. 11, 2013 (KR) .................. 10-2013-0025446
May 29, 2013 (KR) .................. 10-2013-0061051

(51) Int. Cl.
*A45D 40/00*  (2006.01)
*A61Q 19/00*  (2006.01)
(Continued)

(52) U.S. Cl.
CPC ......... *A45D 40/0068* (2013.01); *A45D 34/00* (2013.01); *A45D 40/24* (2013.01);
(Continued)

(58) Field of Classification Search
CPC combination set(s) only.
See application file for complete search history.

(56) References Cited

U.S. PATENT DOCUMENTS 6,056,158 A * 5/2000 Rossetti ............... B67D 7/0216
  222/100
6,883,561 B2   4/2005 Bartholomew et al.
(Continued)

FOREIGN PATENT DOCUMENTS

KR   20-1997-0058267 U    11/1997
KR   10-2004-0030623 A     4/2004
(Continued)

OTHER PUBLICATIONS

International Search Report for PCT/KR2014/002016 dated Jul. 25, 2014 from Korean Intellectual Property Office.

*Primary Examiner* — David Walczak
(74) *Attorney, Agent, or Firm* — Revolution IP, PLLC

(57) ABSTRACT

An instant cosmetic preparation device includes: a housing; a finished product container transfer part which is configured to transfer to a finished product container filled with a cosmetic mixture stored inside the housing to a sealing position; a sealing part which is arranged inside the housing; and a control unit which is arranged inside the housing for controlling the operation of the sealing part to seal an open injection port of the finished product container.

14 Claims, 23 Drawing Sheets

(51) Int. Cl.
  *A61K 8/30* (2006.01)
  *B01F 7/16* (2006.01)
  *B65B 5/04* (2006.01)
  *A45D 34/00* (2006.01)
  *A45D 40/24* (2006.01)
  *B01F 13/10* (2006.01)
  *B01F 15/00* (2006.01)
  *B01F 15/02* (2006.01)

(52) U.S. Cl.
  CPC ............... *A61K 8/30* (2013.01); *A61Q 19/00* (2013.01); *B01F 7/162* (2013.01); *B01F 7/1695* (2013.01); *B01F 13/1061* (2013.01); *B01F 13/1072* (2013.01); *B01F 15/00818* (2013.01); *B01F 15/00876* (2013.01); *B01F 15/0212* (2013.01); *B01F 15/0278* (2013.01); *B65B 5/04* (2013.01); *A45D 2034/005* (2013.01); *A61K 2800/87* (2013.01); *A61K 2800/882* (2013.01); *B01F 2215/0031* (2013.01)

(56) References Cited

U.S. PATENT DOCUMENTS

| | | | | |
|---|---|---|---|---|
| 8,640,432 | B2* | 2/2014 | Rodrigues | B01F 13/1055 141/11 |
| 9,671,795 | B2* | 6/2017 | Igarashi | G05B 15/02 |
| 2001/0047309 | A1 | 11/2001 | Bartholomew et al. | |
| 2003/0062385 | A1 | 4/2003 | Engel et al. | |

FOREIGN PATENT DOCUMENTS

| | | |
|---|---|---|
| KR | 10-0521243 B1 | 10/2005 |
| KR | 20-2011-0005547 U | 6/2011 |
| KR | 10-1299849 B1 | 9/2013 |
| WO | 01-75586 A1 | 10/2001 |

* cited by examiner

INSTANT COSMETIC PREPARATION DEVICE AND THROWAWAY MIXING CONTAINER THEREFOR

CROSS-REFERENCE TO PRIOR PATENT APPLICATIONS

This application is a National Stage Application of PCT International Application No. PCT/KR2014/002016 filed Mar. 11, 2014, which claims priority to Korean Patent Application Nos. 10-2013-0025446 filed Mar. 11, 2013 and 10-2013-0061051 filed May 29, 2013, which are all hereby incorporated by reference in their entirety.

BACKGROUND

The present invention relates to an instant cosmetic preparation device, and in particular to an instant cosmetic preparation device and a throwaway mixing container therefor, wherein a predetermined cosmetic may be instantly manufactured in such a way to selectively agitate a main ingredient and a sub-ingredient of cosmetics provided in the inside or to use previously prepared ampoule.

Most of cosmetics available in markets are mass produced in cosmetic factories. The reasons why such cosmetics are being mass produced only in the cosmetic factories are that only factories which equip with predetermined manufacturing facilities and quality control systems are permitted to manufacture cosmetics, which are regulated in a form of country laws.

Such a mass production method may strictly control qualities in such a way to easily monitor each manufacturing process. If defects occurs in quality of cosmetics, it is possible to easily control such defects through a post-sale management prepared for the sake of defective products.

On the contrary, the mass production method is not actually satisfying customers' various purchase needs and there is still a limit to dynamically cope with such customers' various needs.

To this end, there may be some occasions where a new cosmetic may be developed and sold, which does not substantially reflect a predetermined customer's need or use purpose or a new functional cosmetic may be developed and sold in such a way to newly add only some functional ingredients to the same ingredient.

For this reason, customers may have distrusts on a sale policy of a corresponding cosmetic manufacturing company. In some occasions, customers would manufacture at home in person cosmetics that they want to. Here, according to the manual cosmetic manufacturing method, a user puts cosmetic ingredients, which may well match with his skin or preference, into a mixing container and measures the ingredients with a scale and moves the mixed ingredients into a heating beaker and heats the ingredients on a hot plate or a gas range. The heated ingredients are mixed with a mixing device and are packed in a prepared container for the use.

On the contrary, the above-described method is expensive to manufacture, and it needs to purchase every tool to manufacture cosmetics, which may entail a huge economical burden and complicated purchase procedures, whereupon it is hard for an actual customer to manufacture in person cosmetics and use.

In order to resolve the above-mentioned problems, the Korean utility model publication number 20-2011-0005547 describes a method for mixing cosmetic ingredients in such a way to provide a rotating body in the inside of a storing container.

In the above method, a user, however, needs to measure in person each ingredient and put into a storing container to mix. To this end, an ordinary user, who does not have any professional knowledge, should measure in person each ingredient, which may cause complicated procedures, and finished cosmetics may have bad qualities.

In order for customers to manufacture in person various kinds of cosmetics, it needs to provide systematic education and hands-on sessions based on professional knowledge on the manufacturing of cosmetics, which may be difficult to practically perform.

In order to resolve the above mentioned problems, the same applicant as the present application discloses, in the Korean patent application number 10-2012-0116161 filed on Oct. 18, 2012, an instant cosmetic preparation device wherein a predetermined cosmetic may be manufactured in such a way to instantly agitate a main ingredient and at least one sub-ingredient based on a user's selection.

In the above conventional instant cosmetic preparation device, a user should engage in person a main ingredient container and a sub-ingredient container into an input port of an instant cosmetic preparation device. More specifically, the customer should prepare a main ingredient container, a sub-ingredient container or a finished product container, which means that the above invention provides only a function of a sale assistant device rather than an unmanned vending machine.

SUMMARY

Accordingly, the present invention is made in an effort to resolve the above problems. It is an object of the present invention to provide an instant cosmetic preparation device wherein a main ingredient container, a sub-ingredient container, main ingredients and sub-ingredients all are arranged in the inside, and a corresponding container can be automatically supplied to an agitating position when instantly manufacturing cosmetics, whereupon a customer can instantly manufacture cosmetics that the customer wants to.

It is another object of the present invention to provide an instant cosmetic preparation device wherein if a cosmetic is manufactured as a main ingredient and a sub-ingredient are agitated based on a customer's operation, the opening of a finished product container filled with the thusly instantly manufactured cosmetic can be automatically sealed, and then the finished product can be discharged.

It is further another object of the present invention to provide an instant cosmetic preparation device wherein in a state where a mixing container is placed on the top of a finished product container, the finished product container and the mixing container are rotated at a time toward multiple positions which have been previously set, and then the input, agitation and discharge processes of the sub-ingredient are sequentially performed. When the container moves to the position where it was initially inputted, the manufacturing of the cosmetic is finished.

It is still further another object of the present invention to provide an instant cosmetic preparation device which may allow an ordinary customer to manufacture in person a high quality cosmetic in such a way that an ampoule filled with a predetermined amount of raw ingredients is engaged into an ampoule fitting port provided at a body of a mixing container, and different kinds of ingredients are forced to move through a discharge passage into the inner space of the body, namely, into the inside of the body.

To achieve the above objects, there is provided an instant cosmetic preparation device which may include, but is not limited to, a housing of a given shape; a finished product container transfer part which is configured to transfer to a sealing position a finished product container filled with a cosmetic mixture positioning in the inside of the housing in accordance with a user's control; a sealing part which is disposed in the inside of the housing and is configured to seal an open injection port of the finished product container; and a control unit which is disposed in the inside of the housing and is configured to control the operations of the sealing part so that the injection port of the finished product container can be sealed.

The above-described instant cosmetic preparation device according to the present invention may have advantages below.

First, a main ingredient container into which a main ingredient of a cosmetic and a main ingredient and a sub-ingredient are filled and a sub-ingredient container into which a sub-ingredient having various functions are filled are all disposed in the inside of a housing, and when manufacturing a cosmetic, a corresponding container can be automatically delivered to a sub-ingredient input position and an agitation position.

To this end, even though an instant cosmetic preparation device according to the present invention is installed where a manager or an operation does not stay all the time, a customer may easily and instantly manufacture by himself a cosmetic that the customer wants to.

Second, when a cosmetic is manufactured in such a way that a main ingredient and a sub-ingredient are agitated based on a customer's operation, the opening of a finished product container filled with an instantly manufactured cosmetic can be automatically sealed.

To this end, after the user manufactures an instant cosmetic that we wants to, the finished product container can be perfectly sealed in such a way to engage a stopping cap at the opening of the finished product container or through a heat-treatment process.

Third, in a state where a mixing container is arranged on the top of the finished product container, a previously set cosmetic manufacturing process may be performed in such a way it automatically rotates toward a mixing positing of a sub-ingredient and an agitation and discharge position of a main ingredient and a sub-ingredient, and when it returns back to an initial input position of a finished product container the manufacturing procedure of the cosmetic is finished.

To this end, an inner space of a housing may be efficiently used. An instant cosmetic may be systemically manufactured in such a way to agitate a main ingredient and a sub-ingredient.

Fourth, an ampoule filled with a predetermined amount of raw ingredient is fitted into an ampoule fitting port provided at the body of the mixing container, and different kinds of ingredients are delivered through the discharge passage into the inner space of the body, namely, the inside of the body.

To this end, an ordinary customer without any professional knowledge can manufacture a high quality cosmetic.

BRIEF DESCRIPTION OF THE DRAWINGS

The present invention will become better understood with reference to the accompanying drawings which are given only by way of illustration and thus are not limitative of the present invention, wherein.

DETAILED DESCRIPTION

Figure 1:
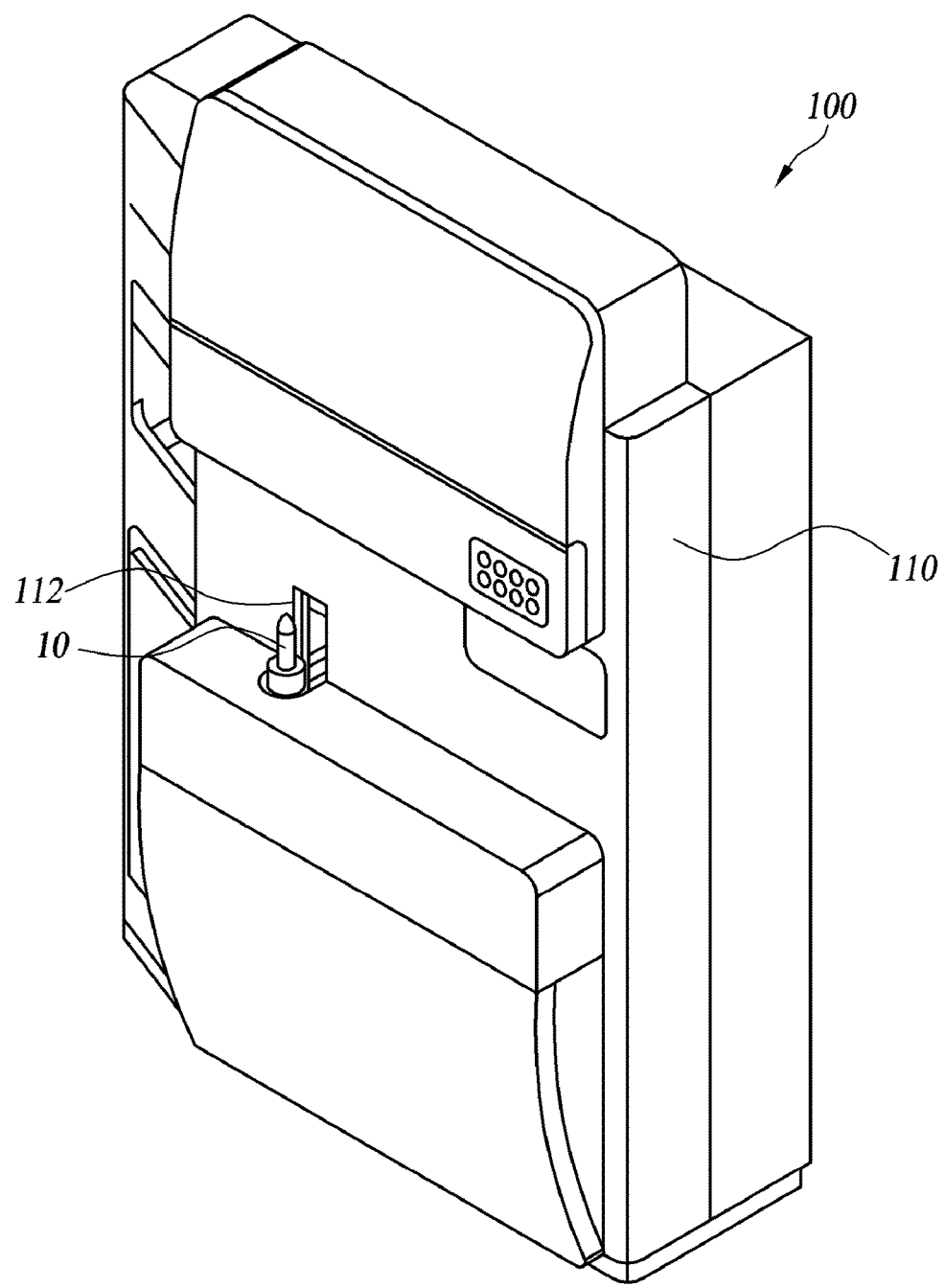
FIG. 1 is a schematic perspective view illustrating the whole exterior of an instant cosmetic preparation device according to an exemplary embodiment of the present invention.

The configuration and operations of the instant cosmetic preparation device according to an exemplary embodiment of the present invention will be described with reference to the accompanying drawings, and then the throwaway mixing container for the thusly manufactured cosmetics according to the present invention will be described.

When assigning the reference numbers, it is noted that the same components will be given the same reference numbers for easier understandings, and even though they are shown on different drawings, they will be given the same reference numbers.

First, as illustrated in FIGS. 1 to 6, the apparatus for instantly manufacturing according to an exemplary embodiment of the present invention may include, but is not limited to, a housing of a given shape 100 which includes at least one or more of a finished product container input port; a panel operation part 110 which is engaged at an outer side of the housing 100 and is configured to select a base ingredient containing a specific natural substance and at least one or more of a sub-ingredient containing a specific functional substance and/or a sealing method; a finished product container transfer part 120 which positions in the inside of the housing 100 and is configured to transfer the finished product container placed on the finished product container input port to a lower end of the position where the base ingredient and the sub-ingredient are agitated; a rotation plate 170 which positions in the inside of the housing 100 and is configured to move it sequentially by dividing into the position where a container filled with a main ingredient mounts on the top, a sub-ingredient delivery position and a main ingredient and a sub-ingredient agitating and discharge position; a mixing container delivery part 130 which positions in the inside of the housing 100, wherein a plurality of mixing containers filled by a predetermined amount with the main ingredient are stacked, the mixing container delivery part being configured to deliver the mixing container to the top of one side of the rotation plate 170; a sub-ingredient delivery part 140 which is configured to deliver at least one or more of the sub-ingredient to the injection port of the mixing container delivered from the mixing container delivery part 130 when the mixing container delivery part 130 moves to the sub-ingredient delivery position with the aid of the movements of the rotation plate 170; an agitating part 150 which is configured to agitate the main ingredient and the sub-ingredient in the mixing container when the mixing container moves to the main ingredient and the sub-ingredient agitating and discharge positions with the aid of the movements of the rotation plate 170 and to discharge to the outside, if necessary; an injection part 160 which position in the inside of the housing and is configured to close the top of the mixing container when the agitating part 150 operates and to press the mixture mixed with the main ingredient and the sub-ingredient to be injected into the finished product container 10 when the operation of the agitating part 150 is completed; sealing parts 180 and 280 which position in the inside of the housing 100 and are configured to seal the injection port of the finished product container 10 transferred in accordance with a control of the finished product container transfer part 120; and a control unit 190 which positions in the inside of the housing 100 and is configured to instantly agitate the main ingredient and the sub-ingredient in accordance with a control command inputted through the panel operation part 110 and to inject the agitated mixture into the finished product container and to seal the injection port of the finished product container and to discharge the same.

The main ingredients which will be used for the instant cosmetic preparation device according to an exemplary embodiment of the present invention may be materials which may determine the kinds of cosmetics, and a skin, an essence, a lotion, a cream, an oil, etc. may be used.

Meanwhile, the sub-ingredients are materials which may be selected based on a customer's preference and may be mixed with the main ingredients. The sub-ingredients include a functional ingredient which may provide special effects or function, for exampoule, a wrinkle improvement, an anticancer effect, a microorganism inhibition agent, etc., a color ingredient which may determine the color of cosmetics, and a perfume ingredient which may determine the smells of cosmetics. For exampoule, there are Siberian ginseng extract, Sngelica gigas extract, acetyl hexa peptide, tocopherol, etc.

The above main ingredients and sub-ingredients are not limited to. It should be understood that since the concept of cosmetic ingredients is very comprehensive, the above-listed kinds are simple suggested as exampoules which might help understandings of the present invention.

As illustrated in FIG. 1, the housing 100 forms the whole exterior of the instant cosmetic preparation device of the present invention and may include, but is not limited to a container fitting part 112 into which a finished product container 10 filled with a cosmetic manufactured by a customer fits, and a panel operation part 110 in which a customer can select a main ingredient, a sub-ingredient and a finished product container 10.

The user selects a mixing container 20 filled with a main ingredient by operating the panel operation part 110 and then selects a sub-ingredient which will be mixed with the main ingredient, thus instantly manufacturing a customized cosmetic which matches with a user's preference and use purpose.

Figure 2:
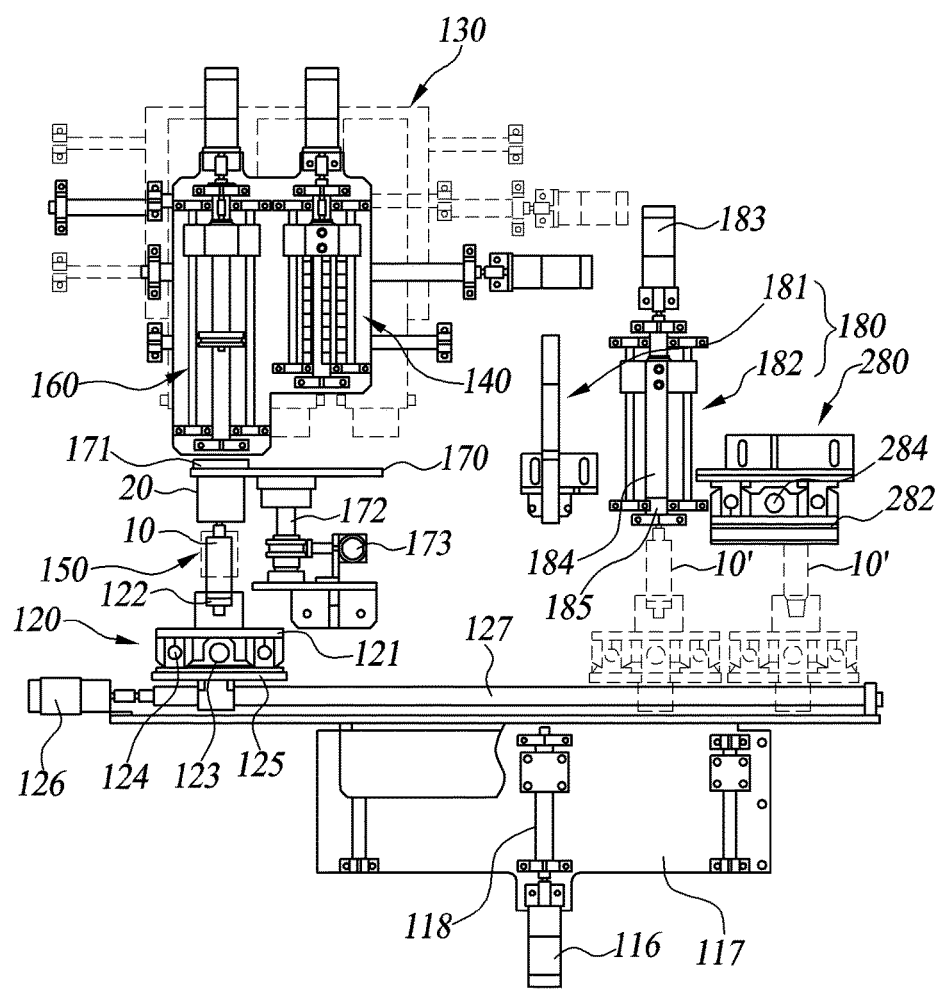
FIG. 2 is a view illustrating an inner configuration of an instant cosmetic preparation device according to an exemplary embodiment of the present invention.

As illustrated in FIG. 2, a product container transfer part 120 is disposed at a lower part of the housing 100, and a finished product container 10 is mounted thereon, into which a main ingredient and a sub-ingredient selected matching with the kinds and function of a cosmetic that the user wants are mixed and are finally stored.

The product container transfer part 120 may include, but is not limited to, a mounting groove 122 which is formed with a predetermined depth for a finished product container 10 to be placed therein; an upper transfer plate 121 which is transferred forward and backward and horizontally along a second screw (not illustrated) by means of the driving of a sixth motor 123; a lower transfer plate 125 which is transferred leftward and rightward and horizontally along the first screw 127 by the driving of a fourth motor 126; a vertical base plate 117 which is fixed at a lower end portion of the upper transfer plate 121; and a horizontal base plate 115 at which a fourth motor 126 is fixed and which linearly move upward and downward and vertically along a third screw 118 with respect to the vertical base plate 117 by the driving of a fifth motor 116.

In addition, the upper transfer plate 121 is configured to rotate, which rotations are limited by the first guide bar 124 provided at both sides and is configured to have only a linear movement in forward and backward and horizontal directions along a second screw (not illustrated) when a sixth motor 123 is driven.

In the same way, the lower transfer plate 125 is also configured to rotate, which rotations are limited by a second guide bar (not illustrated) provided at both sides and is configured to have only a linear movement in leftward and rightward and horizontal directions along a first screw 127 when a fourth motor 126 is driven.

To this end, the product container transfer part 120 may move toward a lower side of an injection part 160 based on the movements in forward and backward and horizontal directions by means of the driving of the fourth motor 126 in a state where the finished product container 10 is mounted in the mounting groove 122, and then a cosmetic agitated with main ingredients and sub-ingredients is stored. The cosmetic is transferred to finishing parts 180 and 280 by the driving of the sixth motor. The open opening of the finished product container 10 is sealed and returns back to the container input port 112 where the customer can take out the finished product container 10 by the driving of the fourth motor 126 and the sixth motor 123.

Figure 3:
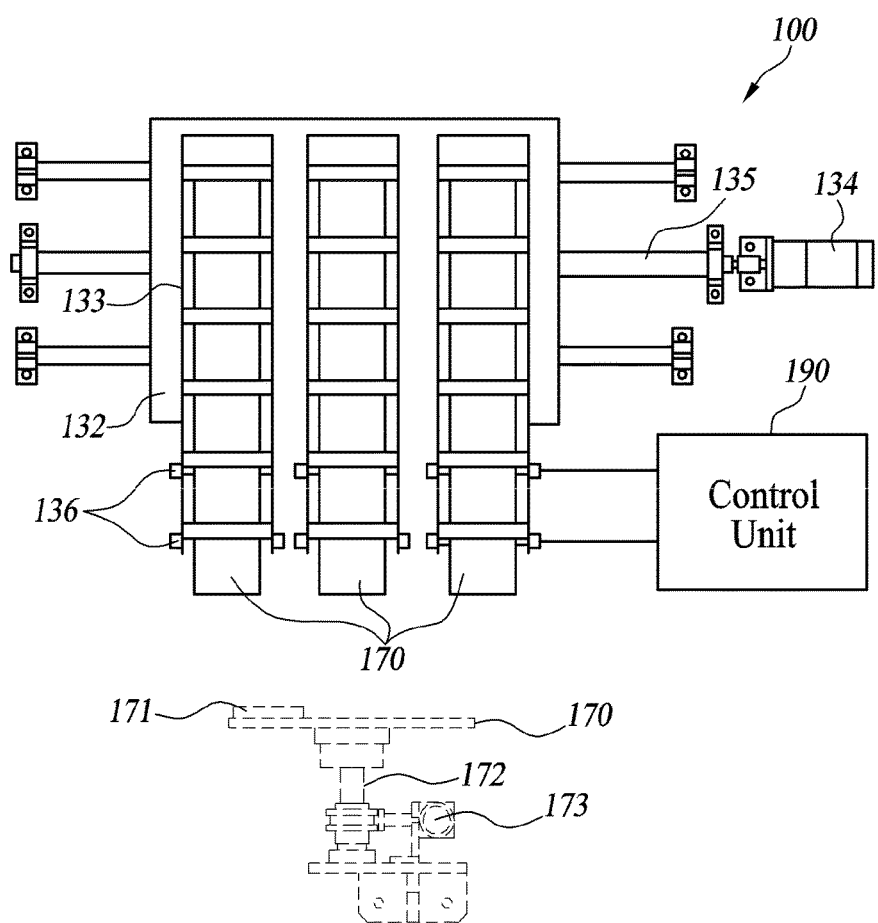
FIG. 3 is a view illustrating a mixing container delivery part of an instant cosmetic preparation device according to an exemplary embodiment of the present invention.

As illustrated in FIG. 3, the mixing container delivery part 130 may deliver the mixing container 20 filled with an ingredient selected by the customer to the container engaging part 171 formed on the top of the rotation plate 170 in accordance with a control of the control unit 190. The mixing container delivery part 130 includes mixing container accommodation parts 133 which are mounted thereon and arranged in multiple rows, and a first vertical tray 132 which is transferred in leftward, rightward and horizontal directions along the fourth screw 135 by the driving of the seventh motor 134.

Each mixing container accommodation part 133 may include, but is not limited to, a plurality of mixing containers 20 which may be stacked in a predetermined direction and may be discharged one by one sequentially, and a first stopper 136 which is disposed at a lower end portion of each mixing container accommodation part 133 so that the mixing containers 20 can be discharged one by one in accordance with a control of the control unit 190.

It is preferred that each mixing container accommodation part 133 is configured to accommodate the mixing containers 20 wherein different kinds of ingredients are filled in each row. For exampoule, a plurality of the mixing containers 20 may be stacked, in which skins may be arranged in the first row, and essences may be arranged in the second row, and lotions may be arranged in the third row.

To this end, if the customer selects a desired main ingredient by operating the panel operation part 110 formed on a front surface of the housing 100, the seventh motor 134 and the first stopper 136 are driven in accordance with a control of the control unit 190, so the first vertical tray 132 moves vertically. To this end, the mixing container accommodation part 133 which is accommodating the mixing container 20 filled with a main ingredient selected by the customer moves to the top of the container engaging part 171 which positions on the top of the rotation plate 170 and may be engaged to the top of the container engaging part 171.

Figure 4:
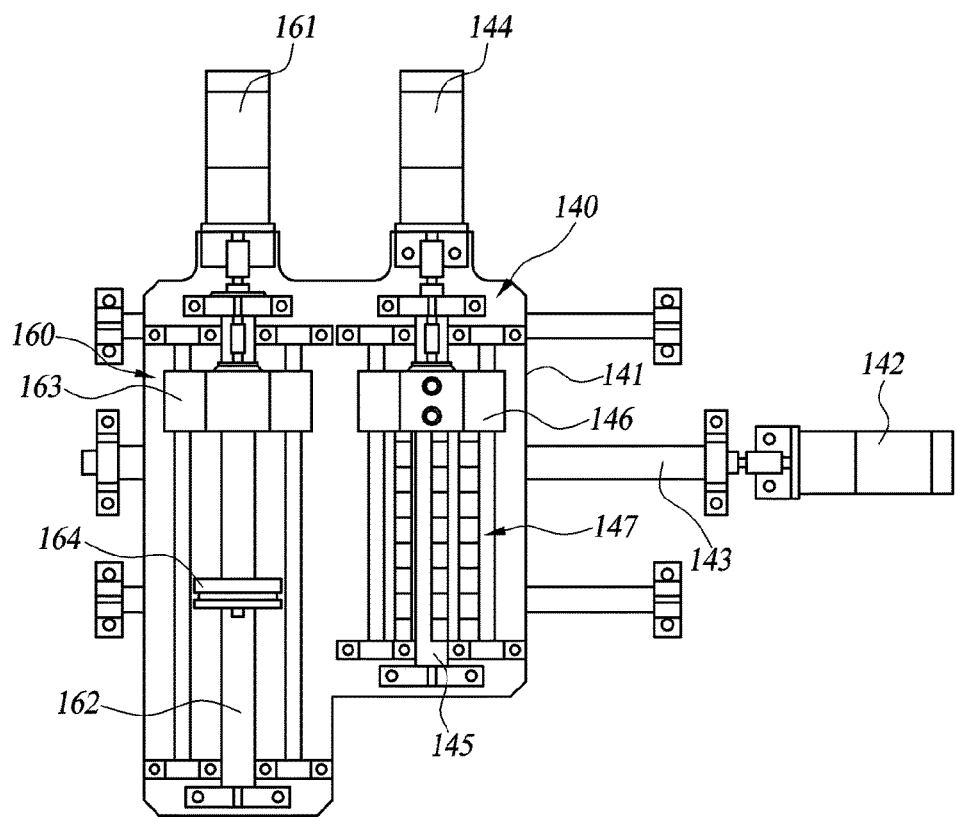
FIG. 4 is a view illustrating an input part and a sub-ingredient delivery part of an instant cosmetic preparation device according to an exemplary embodiment of the present invention.

As illustrated in FIG. 4, the sub-ingredient delivery part 140 allows to deliver the sub-ingredient which is selected by the customer and supplied from the delivery part 130, into the inside of the mixing container 20 engaged to the containing engaging part 171 which positions on the top of the rotation plate 170. The sub-ingredient delivery part 140 may include, but is not limited to, a second vertical plate 141 which is transferred in leftward and right ward and horizontal directions along the fifth screw 143 by the driving of an eighth motor 142; a first transfer body 146 which linearly moves in upward and downward and horizontal directions along the sixth screw 145 by the third motor 144 fixed at one side of the top of the second vertical plate 141 in accordance with a control of the control unit 190; and a sub-ingredient accommodation part 147 wherein a plurality of ampoule type sub-ingredients are stacked inside the first transfer body 146 and which are arranged in multiple rows. It is preferred that different kinds of sub-ingredients are filled in the sub-ingredient accommodation part 147 which position in each row.

To this end, if a customer selects a desired sub-ingredient by operating the panel operation part 110, the mixing container 20 discharged from the mixing container delivery part 130 moves to the lower side of the sub-ingredient delivery part 140 in accordance with a control of the control unit 190. Thereafter, the first transfer body 146 moves in a vertical direction for the lower side of the sub-ingredient accommodation part 147 to approach the top of the mixing container 20 by means of the third motor 144, and the sub-ingredient selected by the customer is injected into the inside of the mixing container 20. To this end, all the main ingredient and the sub-ingredient that the user wants may be accommodated into the inside of the mixing container 20.

Figure 5A:
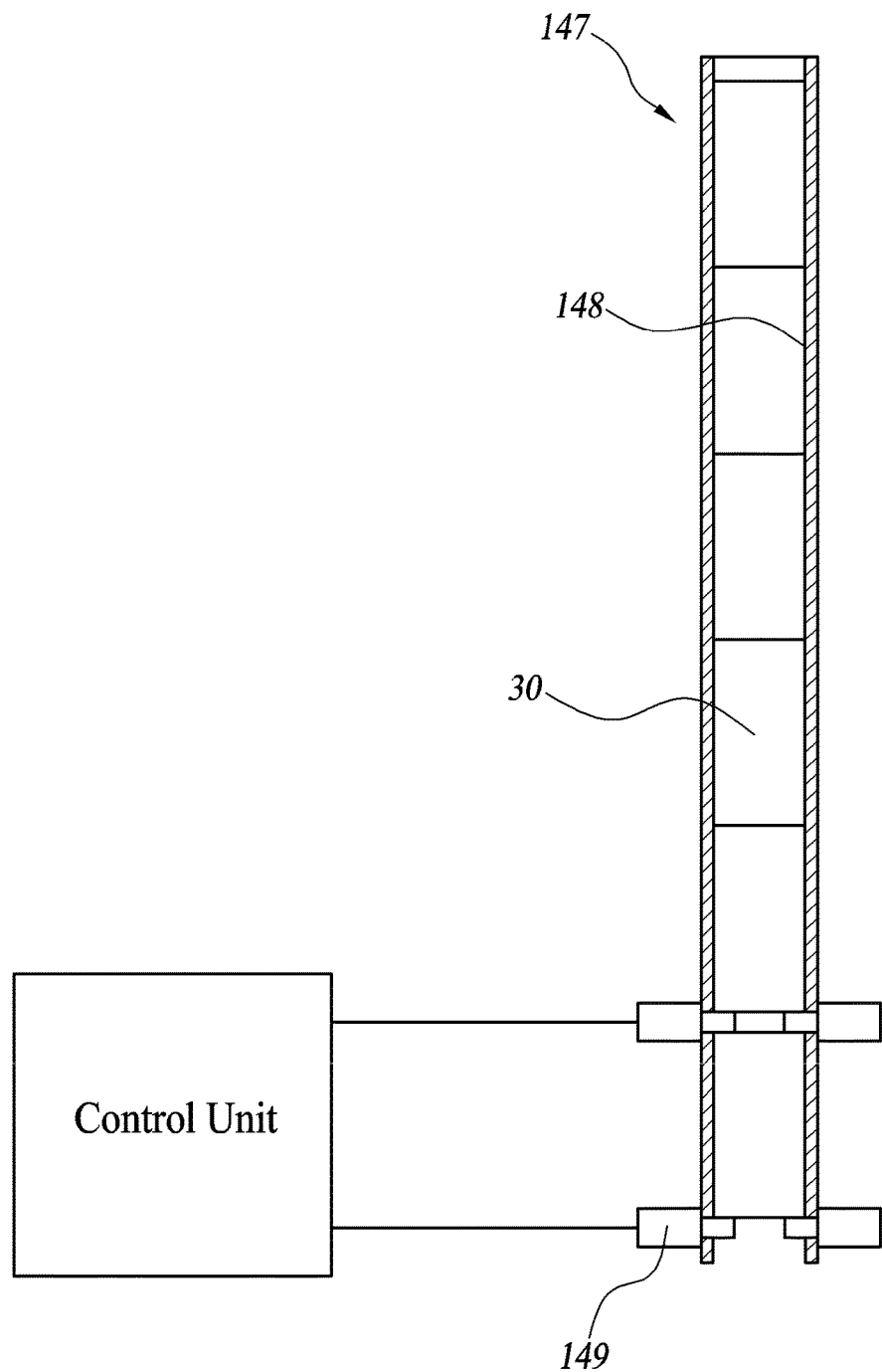
FIGS. 5A and 5B are views illustrating two input methods of a sub-ingredient delivery part of an instant cosmetic preparation device according to an exemplary embodiment of the present invention.

As illustrated in FIG. 5A, in a state where a plurality of ampoule 30 are stacked, which are filled with a predetermined quantity of sub-ingredients in the inside of a hollow cylinder part 148 connected to the first transfer body 146, the sub-ingredient accommodation part 147 according to an exemplary embodiment of the present invention may allow to sequentially discharge the stacked ampoule 20 one by one from the lower most side in such a way to control the operations of the second stopper 149 provided at the lower side of the cylinder part 148.

Figure 5B:
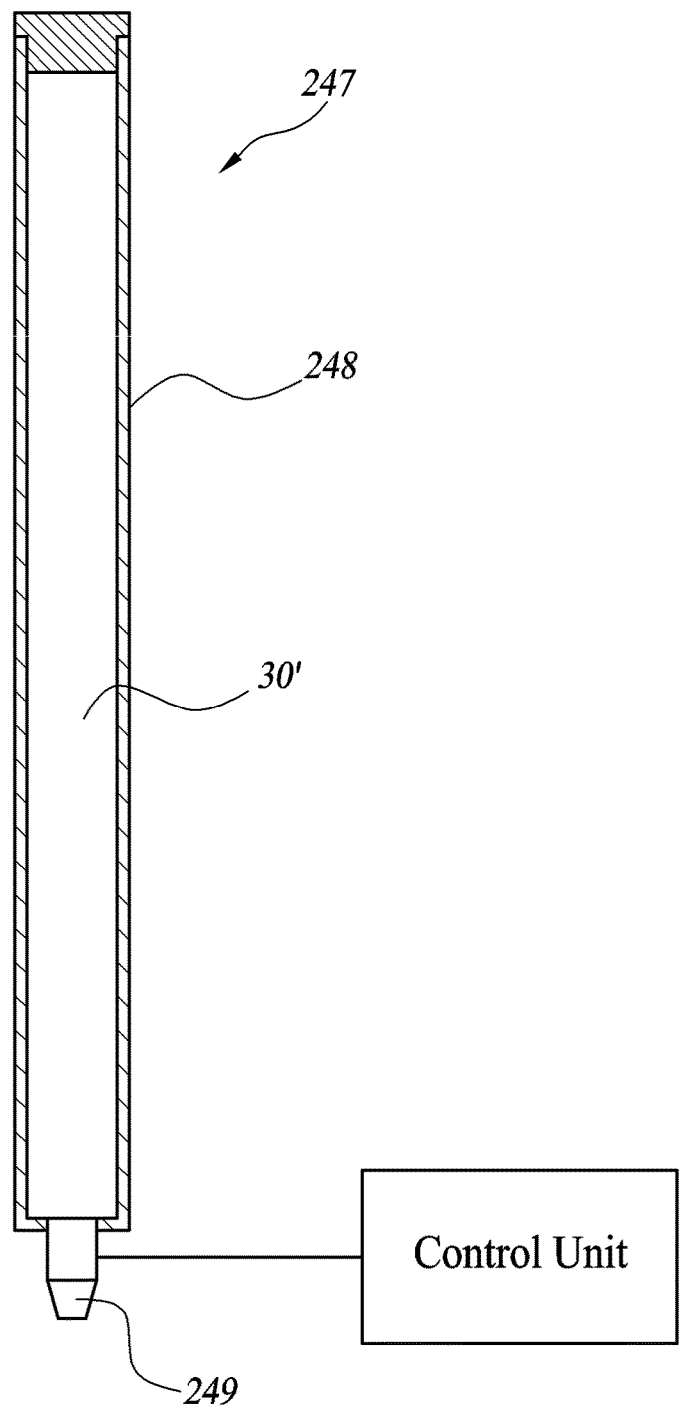

As illustrated in FIG. 5b, there may be provided another type of a sub-ingredient accommodation part 247. It may be configured in such a way that sub-ingredients are accommodated in the hollow cylinder part 248 connected to the first transfer body 146 and the sub-ingredients 30' filled in the inside of a cylindrical body 248 can be sprayed by a predetermined amount through a nozzle 249 disposed at a lower end of the cylinder part 248.

As illustrated in FIG. 4, the injection part 160 is configured to cover the open top of the mixing container 20 while the main ingredient and the sub-ingredient selected by the customer are being mixed by an agitating part 150, and when the mixing is completed, the mixture is injected into the inside of the finished product container 10 by pressing the mixture downward.

The injection part 160 may include, but is not limited to, a second transfer body 163 which is arranged at the second vertical plate 141 and is configured to linearly move in upward and downward and vertical directions along the third screw 162 by the driving of the first motor 161 fixed at one side of the top of the second vertical plate 141; and a plate-shaped pressing plate 164 which is provided at a lower side of the second transfer body 163 and has the roughly same area as the open top of the mixing container 20.

The plate-shaped pressing plate 164 is configured to cover the open part of the mixing container 20 in accordance with a control of the control unit 190 and to press downward the mixture in the inside of the mixing container 20. Namely, when the mixing of a main ingredient and a sub-ingredient filled in the mixing container 20 is completed by the agitating part 150, the second transfer body 163 moves downward by the first motor 161, and the pressing plate 164 provided at a lower end of the second transfer body 163 presses the mixture from its upper side, and the mixture may be injected into the inside of the finished product container 10 through the discharge opening 23 formed at the lower side of the mixing container 20.

Figure 6:
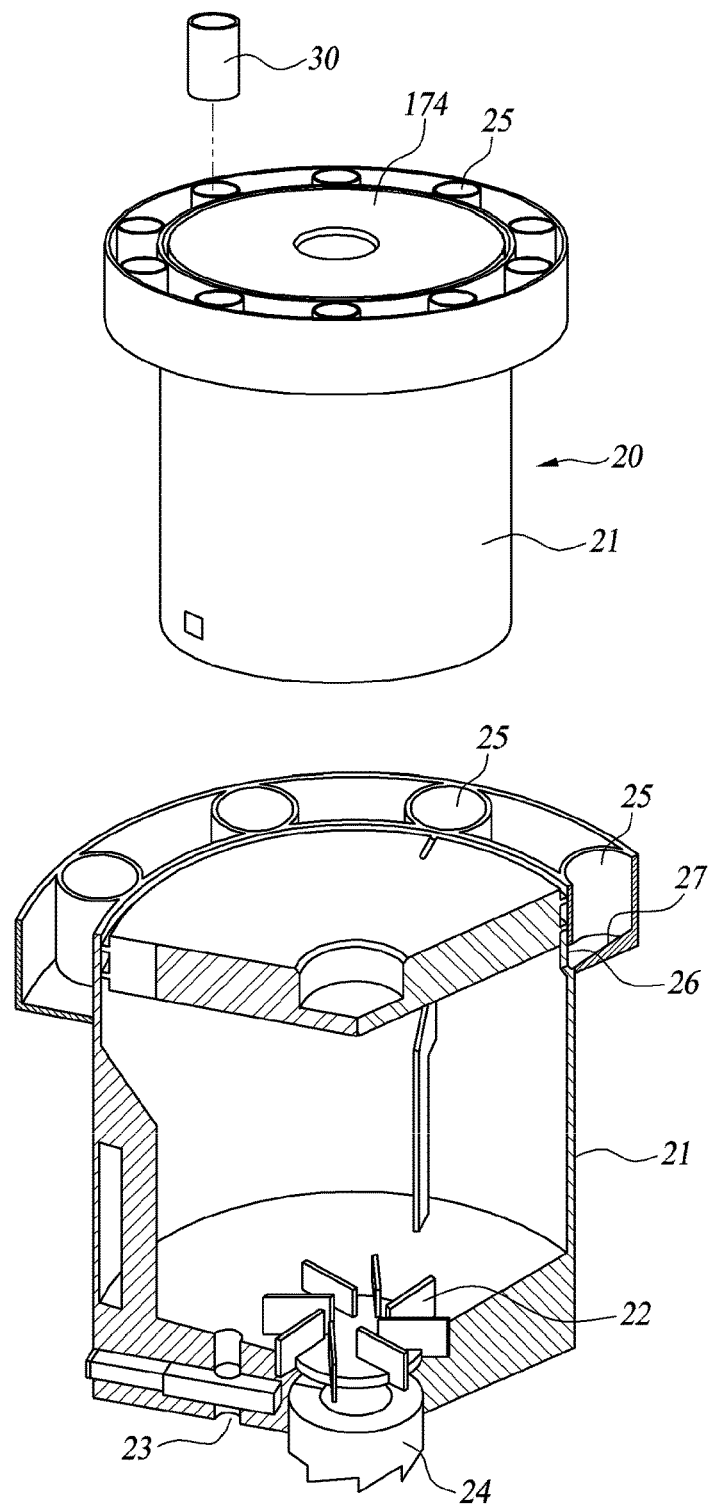
FIG. 6 is a perspective view and cut-away view illustrating a mixing container used in an instant cosmetic preparation device according to an exemplary embodiment of the present invention.

As illustrated in FIG. 6, each mixing container 20 may include, but is not limited to a cylindrical body 21 the top of which is open; an agitating blade 22 which is installed at an underside of the cylindrical body 21 and is configured to rotate in one direction; and a discharge opening 23 which is formed at an underside of the cylindrical body 21.

When a selected sub-ingredient is supplied into the inside of the body 21 through the sub-ingredient delivery part 140, the motor (not illustrated) provided at the agitating part 150 is engaged with the motor engaging part 24 provided at a lower side of the agitating blade 22, whereupon the agitating blade 22 can rotate, thus agitating the main ingredient and the sub-ingredient in the mixing container 20.

Meanwhile, as illustrated in FIG. 5a, if the sub-ingredient delivery part 140 delivers the sub-ingredient in the form of the ampoule 30, the mixing container 20 may be configured in such a way that a plurality of ampoule fitting ports 25 are provided in a surrounding direction at the top of the body 21, so the ampoule 30 filled with the sub-ingredient selected from the cylindrical body 148 can fit into the ampoule fitting port 25. Here, the ampoule fitting port 25 communicates with the inside of the body 21 through a communication port 26, and an edge knife 27 protruding upward by a predetermined length is formed on the bottom surface of the ampoule fitting port 25, whereupon when the ampoule 30 is being fitted, the edge knife 27 breaks the lower side of the ampoule 30, so the sub-ingredient filled in the inside of the ampoule 30 can flow into the inside of the body 21.

However, as illustrated in FIG. 5B, if the sub-ingredient delivery part 140 is configured to form a sub-ingredient in a tube shape, it does not need to form an ampoule fitting port at the top of the mixing container 20. The sub-ingredient may be directly injected into the inside of the mixing container 20 through the nozzle 249 installed at the end portion of one side of the cylindrical body 248.

As illustrated in FIG. 2, the mixing container 20 according to the present invention may be finally discarded after the input of the sub-ingredient, the agitation of the main ingredient and the sub-ingredient and the discharge of the mixture are sequentially performed with the aid of the position movements of the container engaging part 171 based on the rotations of the rotation plate 170 in a state where it is engaged at the container engaging member 171 which is provided at the rotation plate 170.

Figure 7:
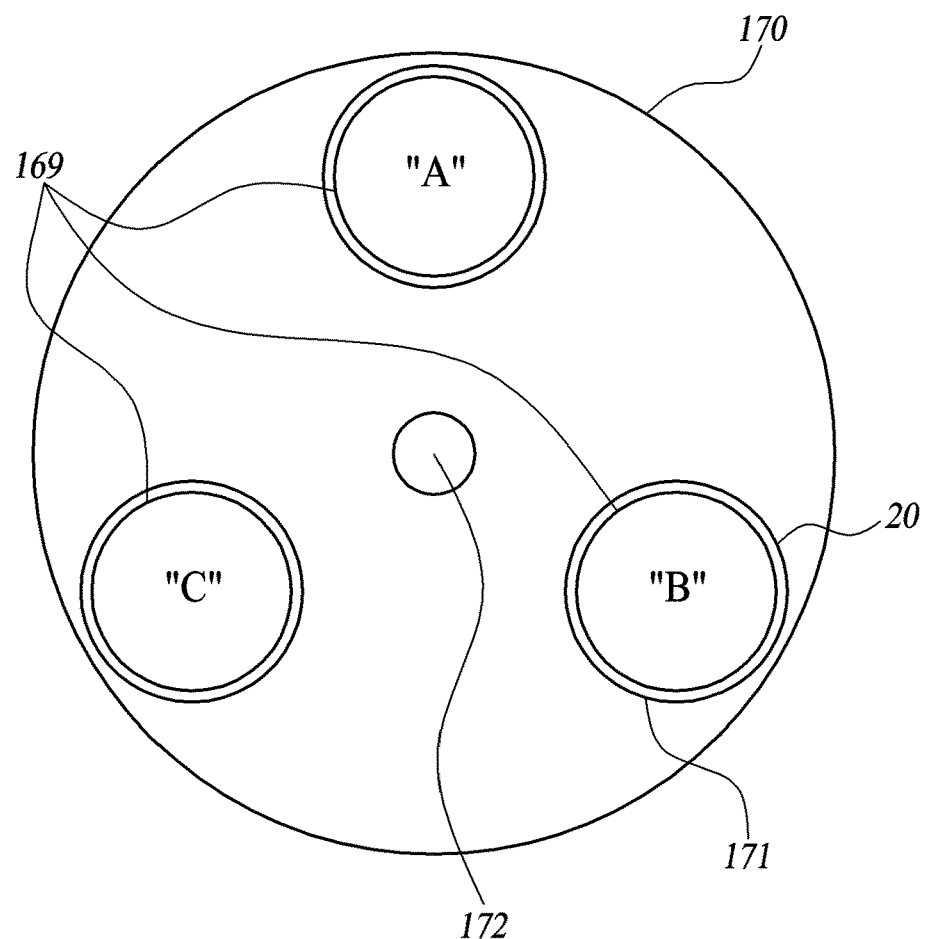
FIG. 7 is a view illustrating a container rotation part of an instant cosmetic preparation device according to an exemplary embodiment of the present invention.
Figure 7:
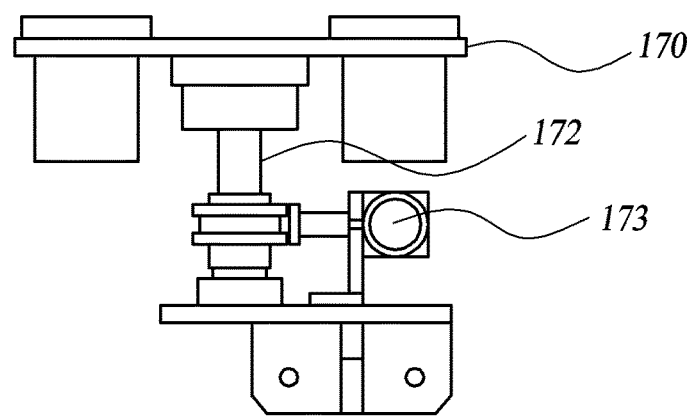

For this, as illustrated in FIG. 7, the rotation plate 170 may include, but is not limited to, a circular plate body 169; a plurality of through container engaging parts 171 which are formed on an outer circumferential surface while being eccentric from the central shaft of the circular plate body 169; and a central shaft 172 which allows to rotate the circular plate body 169 in a predetermined direction with the aid of the second motor 173.

Referring to FIG. 7, the mixing container 20 delivered from the mixing containing delivery part 130 is engaged into the container engaging part 171 in a state where the container engaging part 171 of the rotation plate 170 positions at the lower portion (portion A) of the mixing container delivery part 130 with the aid of the driving of the second motor 173. In addition, the rotation plate 170 rotates by the driving of the second motor 173, and the container engaging part 171 rotates toward the lower portion (portion B) of the sub-ingredient delivery part 140, so the sub-ingredient selected from the sub-ingredient delivery part 140 can be inputted into the inside of the mixing container 20. Thereafter, the rotation plate 170 rotates by the driving of the second motor 173, and the container engaging part 171 rotates toward the lower portion (portion C) of the injection part 16 with the aid of the driving of the second motor 173, so the pressing plate 164 of the injection part 160 will cover the open top of the mixing container 20, and the motor of the agitating part 150 is coupled to the motor engaging part 24 provided at the lower side of the mixing container 20, thus performing the agitating work. Thereafter, when the agitating work is finished, the mixture can be injected into the inside of the finished product container 10 through the discharge opening 23 formed at the lower side of the mixing container 20. When the injection of the mixture into the finished product container 10 is completed, the used mixing container 20 is separated from the engaging part 171 and is discharged into a collection container (not illustrated) which is provided separate.

Meanwhile, the first and second finishing parts 180 and 280 are configured to seal the open top of the finished product container 10 into which the mixture mixed with the main ingredient and the sub-ingredient has been injected through the injection part 160. After the mixture is injected into the finished product container 10 through the discharge opening 23 of the mixing container 20, the finished product container in which the mixture was injected is transferred to one previously set finishing part, in accordance with a control of the control unit 190, among the first and second finishing parts 180 and 280 by the product container transfer part 120 in accordance with a control of the control unit 19 to correspond to the sealing method selected by the user on the panel operation part 110.

The above first finishing part 180 allows to engage the inner cap on the injection port of the finished product container 10, and the second finishing part 280 allows to seal the injection port of the finished product container 10.

The first finishing part 180 may include, but is not limited to, an inner cap delivery part 181 wherein a plurality of inner caps are stacked in a predetermined direction, and the inner caps are temporarily fixed at the open top of the finished product container 10 in accordance with a control of the control unit 190; an inner cap engaging part 182 which is configured to move the finished product container 10 wherein the inner caps are temporarily fixed by the driving of the fourth motor 126, to the engaging position of the inner cap; a road 184 which may move upward and downward by the operation of a ninth motor 183 provided at the inner cap engaging part 182; and a cap pressing plate 185 which is provided at a lower side of the rod 184 and is configured to seal the open top of the finished product container 10 by pressing the temporarily fixed inner cap.

In addition, the second finishing part 280 may include, but is not limited to, a fourth motor 146 at one side of which an inner cap and an outer cap are engaged, and at the other side of which is open, thus moving the product container 10'; and a pair of heat plates 282 which may move by a tenth motor 284 and are configured to seal the open portion of the product container 10' by providing heat from both sides.

The finished product containers 10 and 10' the open tops of which have been completely sealed may move toward the input part 112 with the aid of the product container transfer part 120, so the customer can take out the finished product containers 10 and 10' filled with finished cosmetics.

The operation sequences of the instant cosmetic preparation device according to an exemplary embodiment of the present invention will be described with reference to FIGS. 8A to 8F.

Figure 8A:
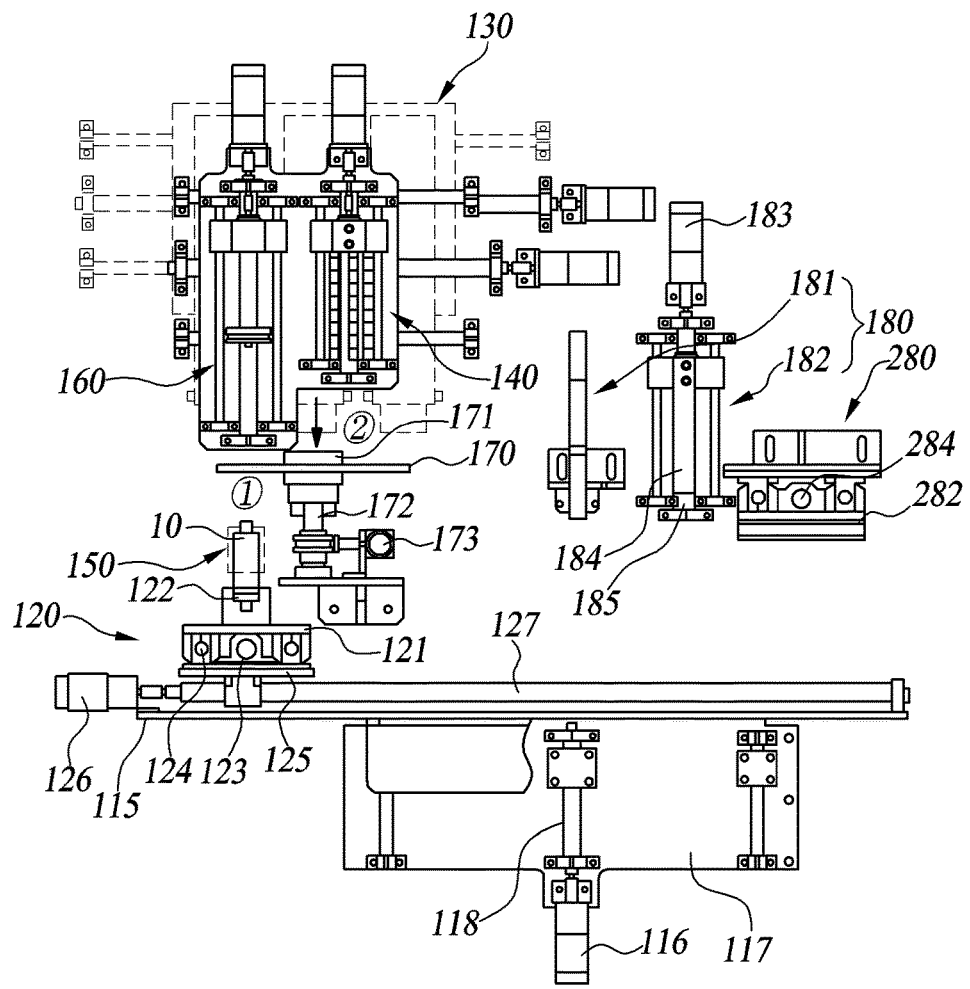
FIGS. 8A to 8F are views for sequentially describing an operation sequence of an instant cosmetic preparation device according to an exemplary embodiment of the present invention.

First, the customer fits the finished product container 10 into the mounting groove 122 of the product container transfer part 120 and selects a desired main ingredient and a sub-ingredient on the panel operation part 110 provided on the front side of the housing 100 (refer to FIG. 8A).

When the selection of the main ingredient and the sub-ingredient that the customer wants is finished, the finished product container 10 moves into the inside of the housing 100 with the aid of the movement of the product container transfer part 120, and in the mixing container delivery part 130, the mixing container 20 which stores the main ingredient selected by the customer is discharged from the mixing container accommodation part 133 and is engaged into the container engaging part 171 of the rotation plate 170.

Here, the first vertical ray 132 moves by the driving of the seventh motor 134, and the lower side of the mixing container accommodation part 133 wherein the mixing containers 20 filled by a predetermined amount and with a main ingredient selected by the customer are stacked moves toward the top of the container engaging part 171, and the selected mixing container 20 is engaged into the container engaging part 171.

Figure 8B:
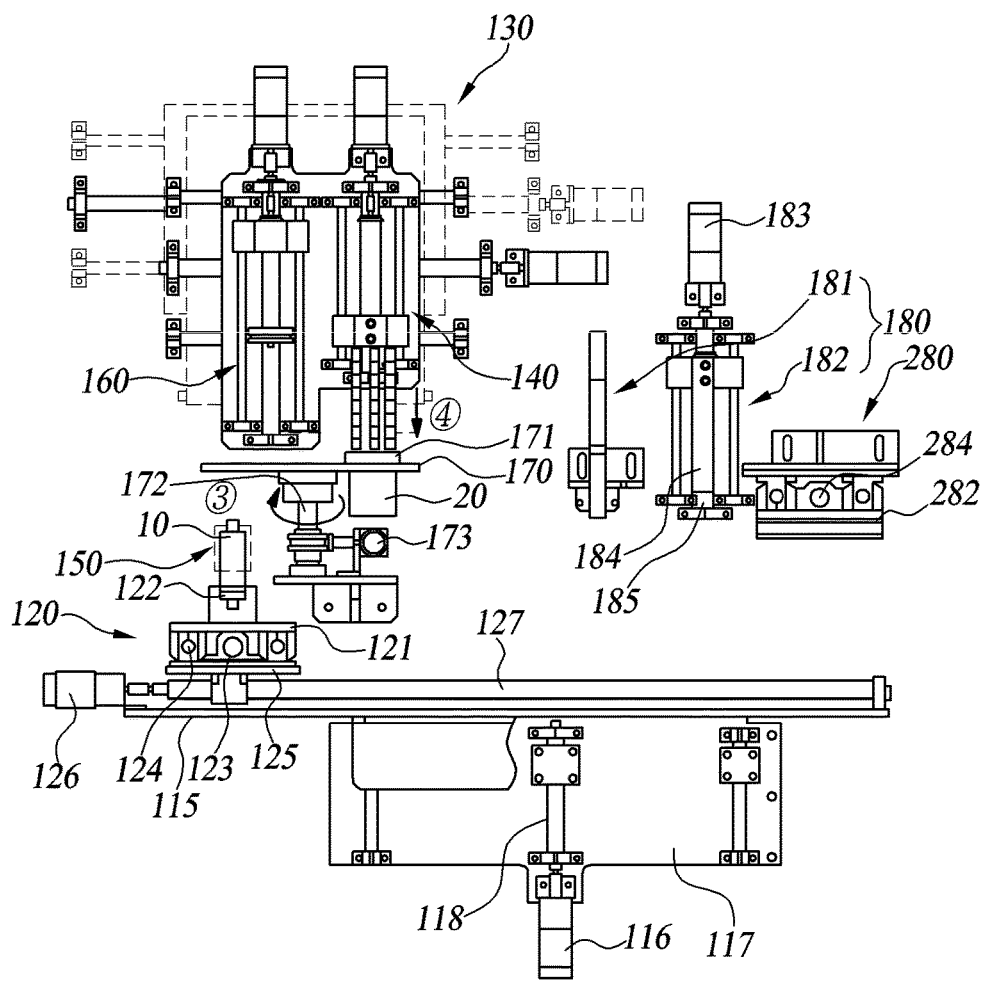

Thereafter, the rotation plate 170 may rotate in one direction by the driving of the second motor 173, and the mixing container 20 engaged in the container engaging part 171 and the finished product container 10 positioning at the lower side concurrently rotate toward the sub-ingredient delivery portion (portion B in FIG. 7), and the sub-ingredient selected by the customer is delivered into the inside of the mixing container 20 through the sub-ingredient delivery part 140 (refer to FIG. 8B). Here, it is preferred that the sub-ingredients selected by the customer may be at least one or more, multiple, in number.

When the sub-ingredient is delivered into the inside of the mixing container 20, the rotation plate 170 rotates, and the mixing container 20 engaged into the container engaging part 171 and the finished product container 10 positioning at the lower side concurrently rotate toward the agitating and discharge openingions (portion C in FIG. 7), and in the injection part 160, the second transfer body 163 moves downward by the driving of the first motor 161, so the pressing plate 164 can cover the open top of the mixing container 20. At the same time, the motor provided at the agitating part 150 is coupled to the motor engaging part 24 provided at the lower side of the mixing container 20, thus rotating the agitating blade 22 provided in the inside of the mixing container 20, whereby the agitating work of the main ingredient and the sub-ingredient selected by the customer is performed.

Figure 8C:
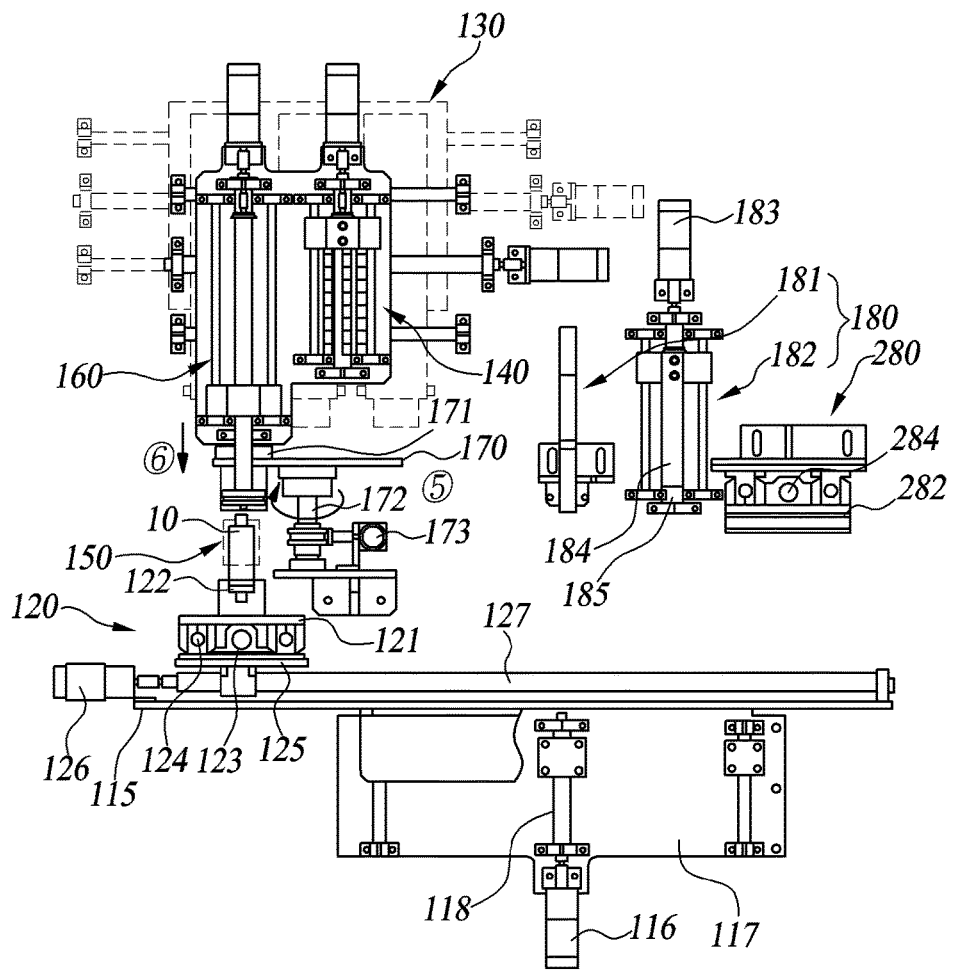
Figure 8D:
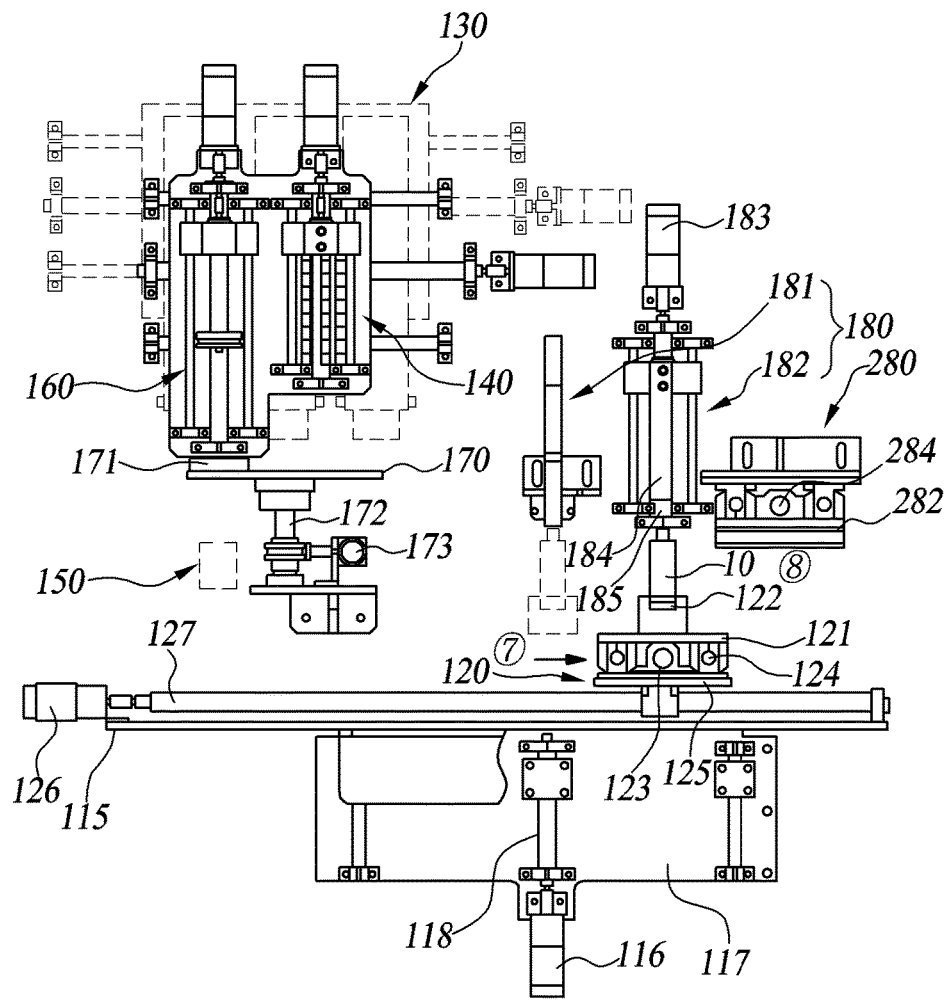

Thereafter, when the agitating work is finished, the upper transfer plate 121 moves to the lower side of the mixing container 20 by the driving of the sixth motor 123, and the mixture is pressed by the pressing plate 164 and can be injected into the inside of the finished product container 10 through the discharge opening 23 formed at the lower side of the mixing container 20 (refer to FIG. 8C).

Thereafter, the finished product container 10 into which the mixture was injected moves toward the first and second finishing parts 180 and 280 with the aid of the movements of the product container transfer part 120.

Figure 8E:
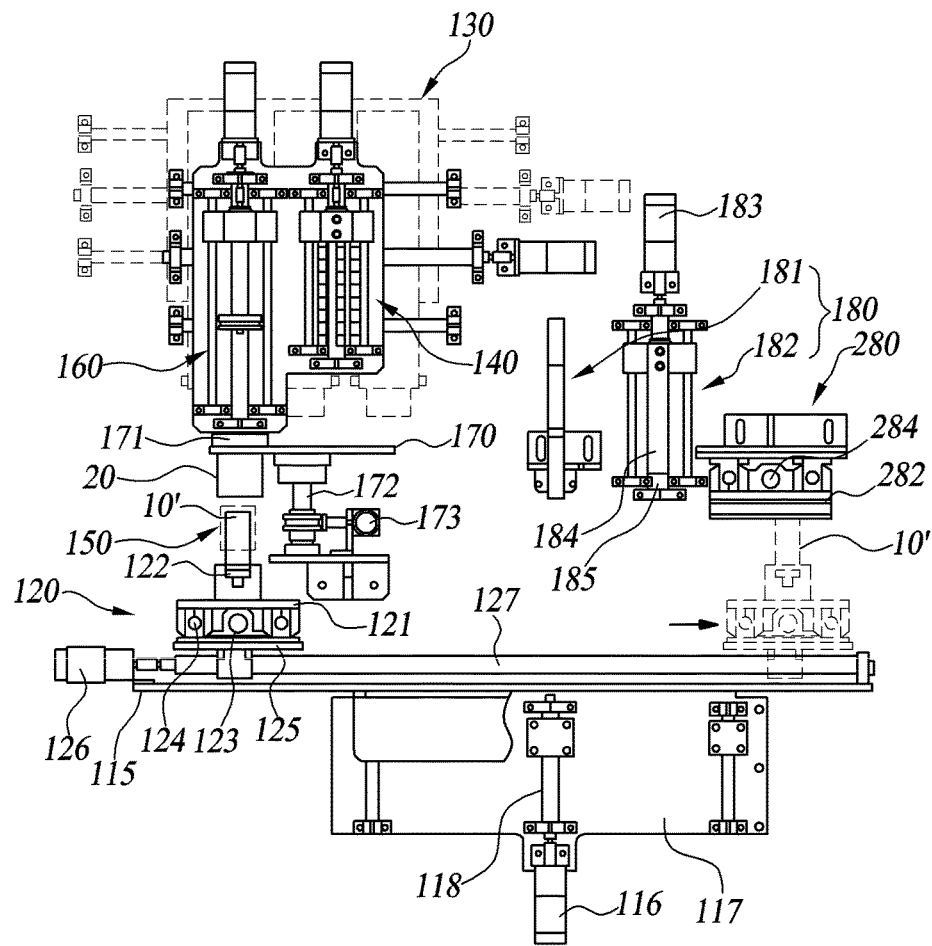

At this time, the inner cap may be engaged to the open injection port of the finished product container 10 into which the mixture was injected (refer to FIG. 8D) or the open injection port of the finished product container 10' into which the mixture was injected may be sealed by the heat plate 282 (refer to FIG. 8E).

Figure 8F:
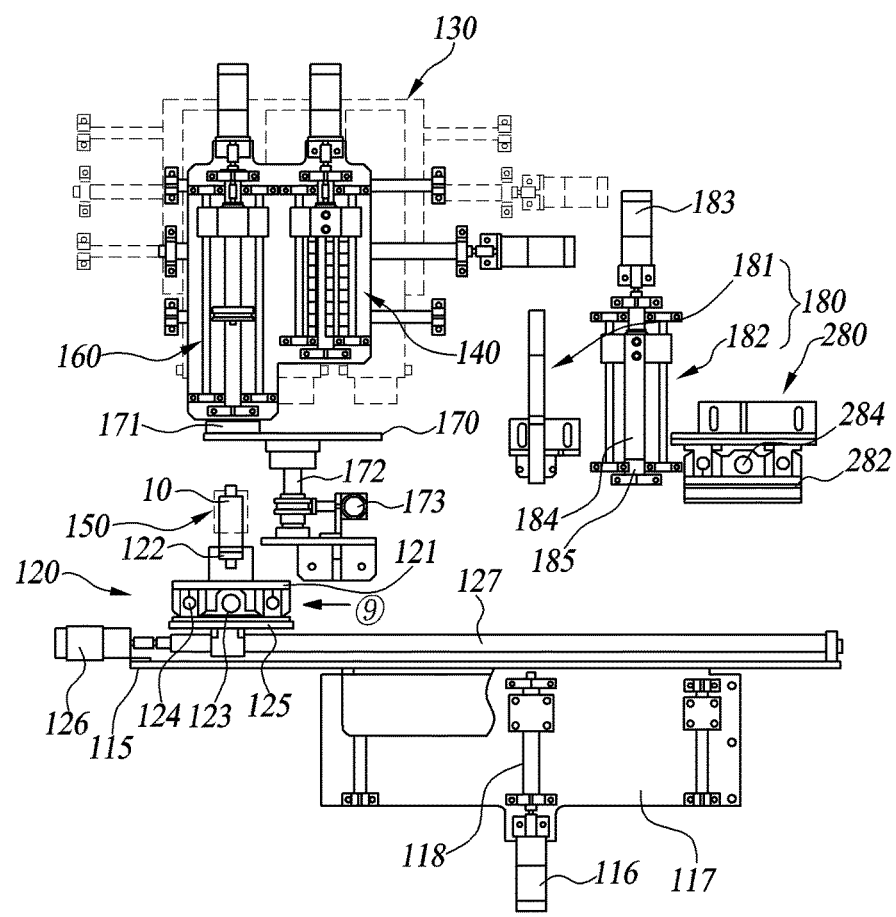

Thereafter, the finished product containers 10 and 10' may be moved toward the input port 112 of the housing 100 by means of the product container transfer part 120, so the customer can take out the finished product (refer to FIG. 8F).

Next, the throwaway cosmetic mixing container 30 according to another exemplary embodiment of the present invention may be used for the instant cosmetic preparation device which is configured to manufacture cosmetics in such a way to instantly mix different kinds of cosmetic ingredients. The ampoule 30 filled with cosmetic ingredients is coupled to the ampoule fitting part 312, and the ingredients stored in the ampoule is inputted into the inside of the body 310, thus easily mixing them using the mixing part 320 engaged at the body 310, which makes it possible to instantly manufacture high quality cosmetics, which is a key technical feature of the present invention.

The Korean patent application number 10-2012-0116161 which was filed by the applicant of the present application may be adapted as an exampoule so that the instant cosmetic preparation device can manufacture a finished cosmetic in such a way to mix the selected ingredients in the mixing container after various kinds of ingredients are selected. It is obvious that the inner structure of the instant cosmetic preparation device of the patent may be appropriately modified into a predetermined form to match with the throwaway cosmetic container according to the present invention.

As illustrated in FIGS. 9 to 14, the throwaway cosmetic mixing container 100 according to the present invention may include, but is not limited to, a body 310, a mixing part 320 and an opening and closing part 330.

The body 310 may be configured to provide a space wherein two or more than two kinds of different ingredients can be mixed and may be formed in a box shape having an inner space the top of which is open. At least one discharge hole 314 is through formed at a lower side so as to discharge to the outside a cosmetic which is mixed in the inner space. In addition, the body 310 may include a plurality of ampoule insertion holes 312 along an open upper rim. The above amply fitting part 312 is provided to engage the ampoule 30 in which the ingredients of the cosmetics are previously stored, into the body 310. The ampoule fitting part 312 is grooved with a predetermined depth from the upper surface to the downward direction so as to fixedly fit the ampoule 30.

Figure 9:
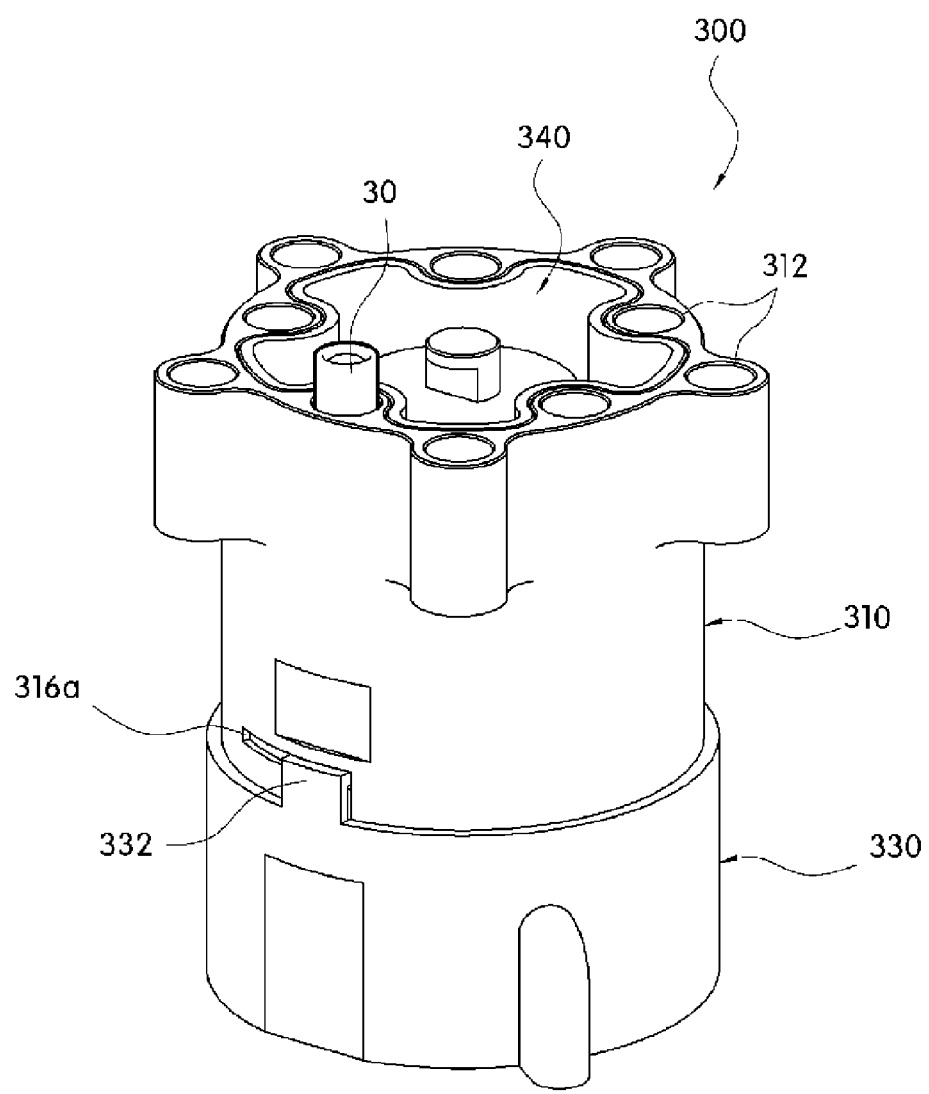
FIG. 9 is a perspective view illustrating the whole configuration of an instant cosmetic preparation device according to another exemplary embodiment of the present invention.
Figure 10:
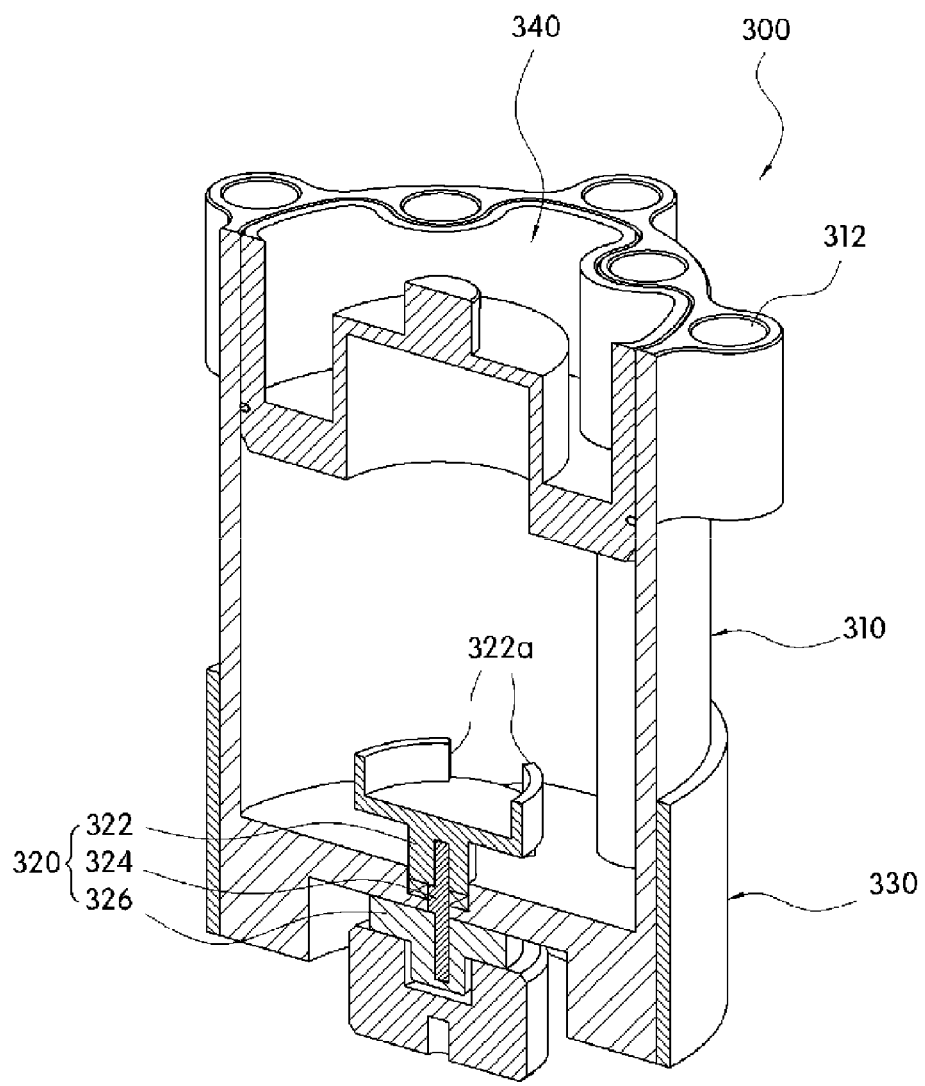
FIG. 10 is a cross sectional view illustrating an engaged state in FIG. 9.
Figure 11:
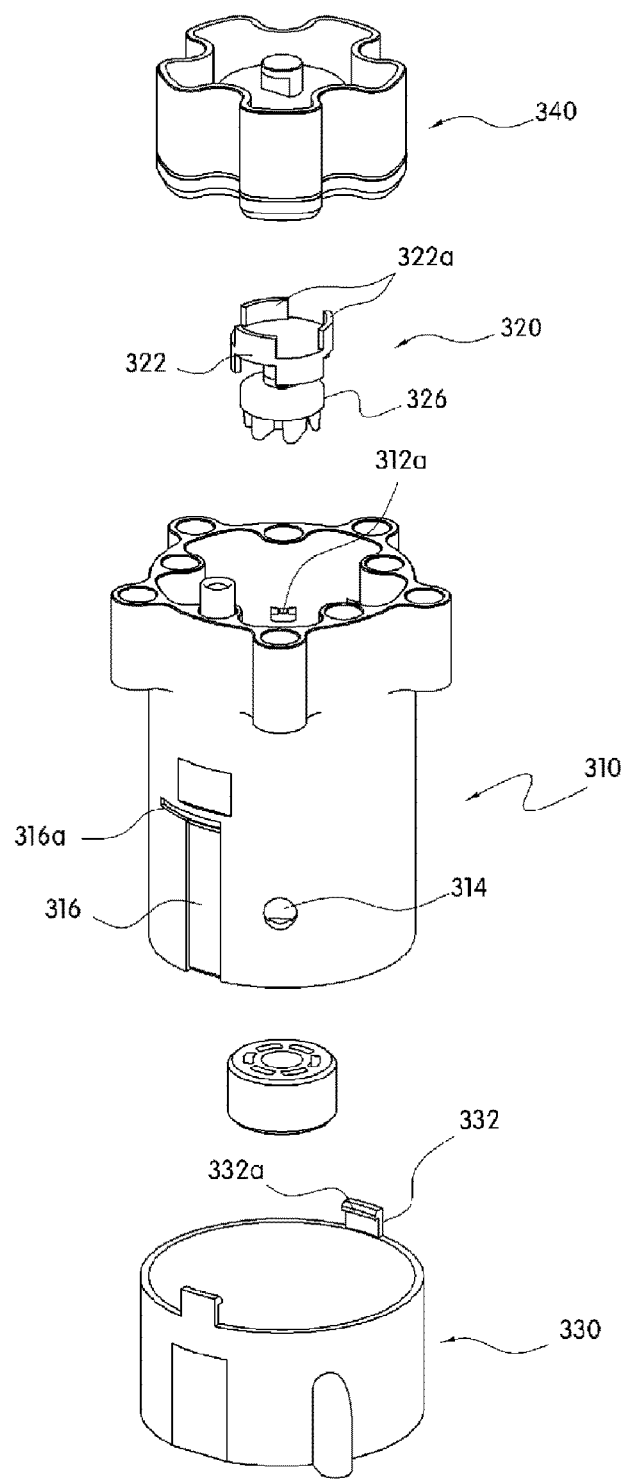
FIG. 11 is a perspective view illustrating a disassembled state in FIG. 9.

Here, as illustrated in FIG. 9, a plurality of the ampoule insertion holes 312 are alternately formed on an inner side and an outer side along a circle rim which may be virtually drawn. To this end, a concave portion and a convex portion are repeatedly formed on an inner surface of the body 310. The outer surface of the pressing part 340 coupled through the open upper side of the body 310 is configured to have the same shape as the inner surface of the body 310. With the aid of the above arrangement, the moving route of the pressing part 340 may be guided while the pressing part 340 coupled to the top of the body 310 is moved to the downward direction so as to discharge to the outside the cosmetic mixed by the mixing part 320 in the inside of the body 310. In addition, the convex portion protruding inward of the body 310 may allow the mixing to take place well in such a way to disturb the movements of the ingredients which are mixed when mixing the ingredients by the mixing part 320.

Meanwhile, the drawings show that the ampoule insertion holes 312 are alternately formed on the inner side and the outer side along a virtual circular rim, and a concave portion and a convex portion are repeatedly formed on the inner surface of the body 310, but it is not limited thereto. The amply fitting parts 312 may be arranged only on the outer side along the virtual circular rim, and a plurality of disturbing plates protruding inward along the height direction may be provided on an inner surface of the body 310, thus enhancing the mixing of the ingredients. Namely, the convex portion and the disturbing plates may be formed protruding inward along the height direction on the inner surface of the body so as to make the ingredients collide with each other with the aid of the convex portion and the disturbing plate while the ingredients are being rotated by centrifugal force when mixing at least two kinds of ingredients by the mixing part, thus obtaining the function of the disturbing part which is configured to prevent any idle rotations, which may result in better agitation.

Here, the ampoule 30 may be formed by covering the contents corresponding to the ingredient of a cosmetic with a thin outer skin. The above contents may be any of a base ingredient, a sub-ingredient and a functional ingredient which form the cosmetic. Furthermore, it is obvious that the ampoule 30 which fits into the amply fitting part 312 after a predetermined amount of the base ingredient is previously stored in the inner space of the body 310 may be formed of a sub-ingredient or a functional ingredient which may be added to the base ingredient, so the ampoule can be used in a type wherein it is mixed in the inner space of the body 310.

In addition, the drawings show that the ampoule fitting part 312 is integrally formed along the upper rim of the body 310, but it is not limited thereto. It is obvious that a separate member having the ampoule fitting part 312 mat be engaged detachable to the open top of the body 310.

Figure 12:
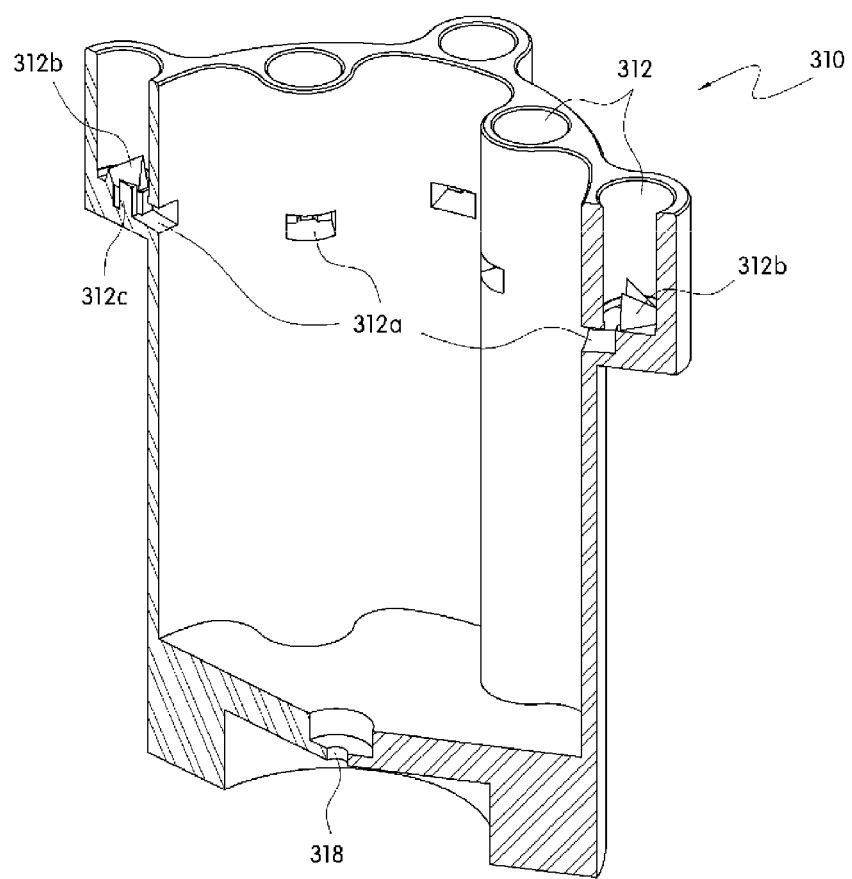
FIG. 12 is a perspective view when seeing from the top a throwaway cosmetic mixing container in FIG. 9.

Referring to FIG. 12, at least one discharge passage 312a communicating with the inner space of the body 310 may be provided on the bottom surface of the amply fitting part 312. The above discharge passage 312a is a moving passage through which the contents which may become ingredients of a cosmetic stored in the ampoule 30 can be provided into the inner space of the body 310.

In addition, at least one knife blade 312b protruding at a predetermined height may be provided on the bottom surface of the ampoule fitting part 312. This knife blade 312b is configured to cut away the lower side of the ampoule 30 engaged in the amply fitting part 312, so the contents stored in the inside of the ampoule 30 can be discharged to the outside through the portion cut-away by the knife blade 312b. To this end, the contents stored in the ampoule 30 can be discharged to the outside of the ampoule 30 through the portion cut-away by the knife blade 312b, and then can be inputted into the inner space of the body 310 through the discharge passage 312a formed on the bottom surface of the ampoule fitting part 312. At this time, the discharge passage 312a is formed gradually inclining downward from the outside to the inside of the body, whereupon the contents discharged from the ampoule 30 can easily move along the discharge passage 312a into the inner space of the body 312.

Figure 13:
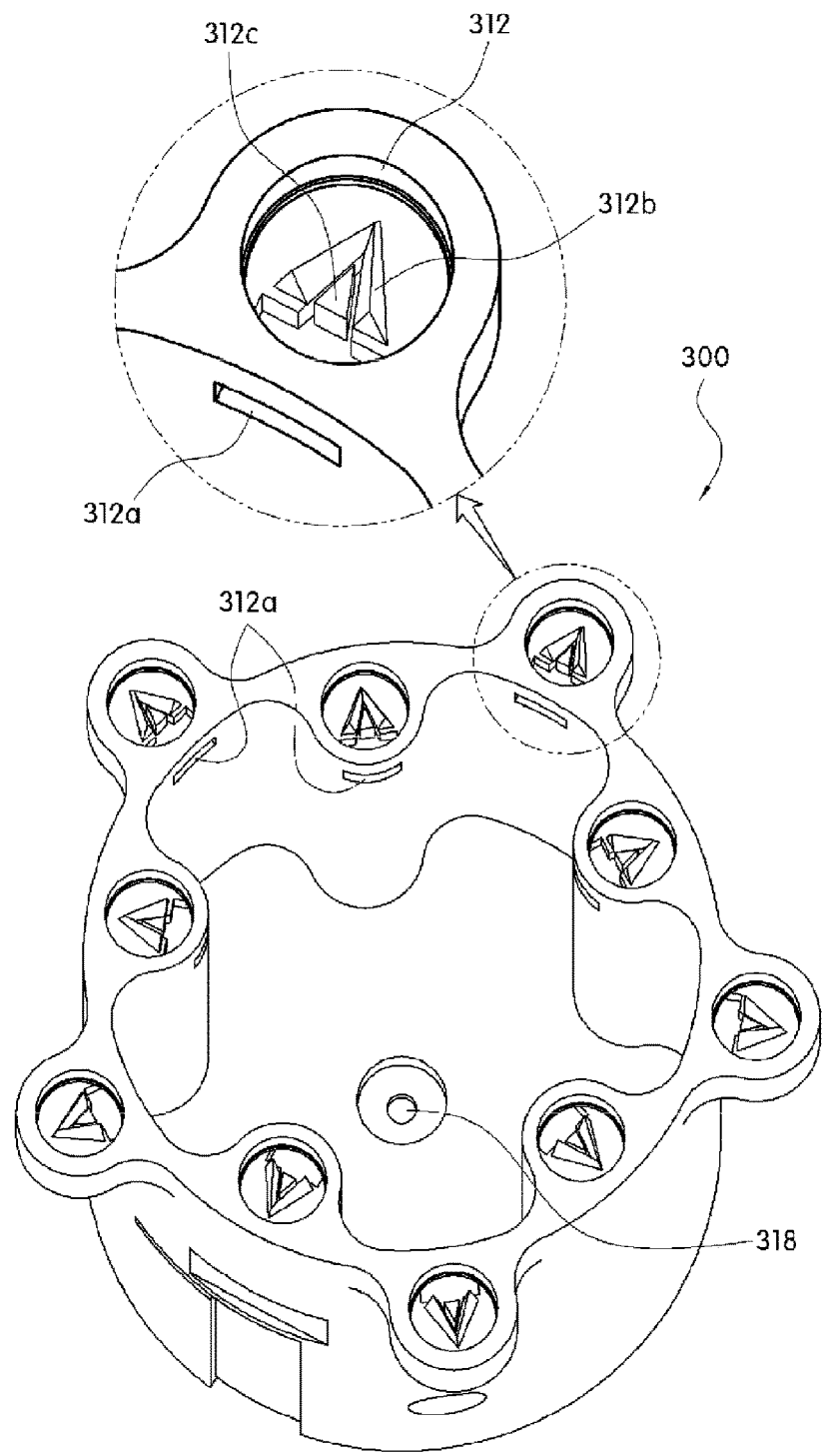
FIG. 13 is a cut-away view illustrating the inside of a body in FIG. 9.

Here, in a state where the ampoule 30 is fit in the ampoule fitting part 312, the upper side of the ampoule is pressed toward the lower side by external force, so the lower side can be cut away by the knife blade 312b. At this time, as illustrated in FIGS. 12 and 13, the knife blade 312b may be formed in a V-shape the intermediate portion of the length of which is bent and may include a protruding part 312c which is formed at a bent inner side and has a predetermined height. With the aid of the above protruding part 312c, the moving passage of the contents which are discharged to the outside of the ampoule 30 through the portion cut-away by the knife blade 312b can be limited to both sides of the protruding part 312c, whereupon the contents can be more efficiently moved into the inner space of the body 310 through the discharge passage 312a.

The mixing part 320 is disposed in the inner space of the body 310 so as to mix different kinds of cosmetic ingredients. The mixing part 320 may include a rotation blade part 322 which equips with a plurality of blades 322a which are alternately arranged at upper sides and lower sides with respect to the horizontal surface along the rim with predetermined heights and is engaged rotatable to the bottom surface of the body 310; and a motor engaging part 326 which is engaged to the rotation blade part 322 through an engaging shaft 324 and is arranged at an outer side of the body 310 and is engaged with an external motor (not illustrated). Here, the engaging shaft 324 interconnecting the rotation blade part 322 and the motor engaging part 326 is arranged and inserted into the engaging hole 318 which is through formed on the bottom surface of the body 310. The engaging shaft 324 may be formed in such a way that its intermediate portion has a diameter wider than the diameter of the engaging hole 318, thus preventing any separation from the engaging hole 318 while preventing the rotation blade part 322 from moving in upward and downward directions, whereby the rotation blade part 322 can smoothly rotate in the inner space of the body 310.

Meanwhile, the motor engaging part 326 engaged to the lower side of the engaging shaft 324 may provide a driving force to rotate the rotation blade part 322 so as to mix various kinds of cosmetic ingredients which are inputted into the inner space. Such a motor engaging part 326 may be engaged with an external motor (not illustrated) through a separate coupler which is engaged to its lower side, thus receiving driving force from the motor.

The drawings show that the rotation blade part 322 and the motor engaging part 326 are engaged through the engaging shaft 324, but it is not limited thereto. It is obvious that they may be directly connected in such a way that the rotation blade 322 and the motor engaging part 326 are shape-matched without using the engaging shaft 324.

Figure 14:
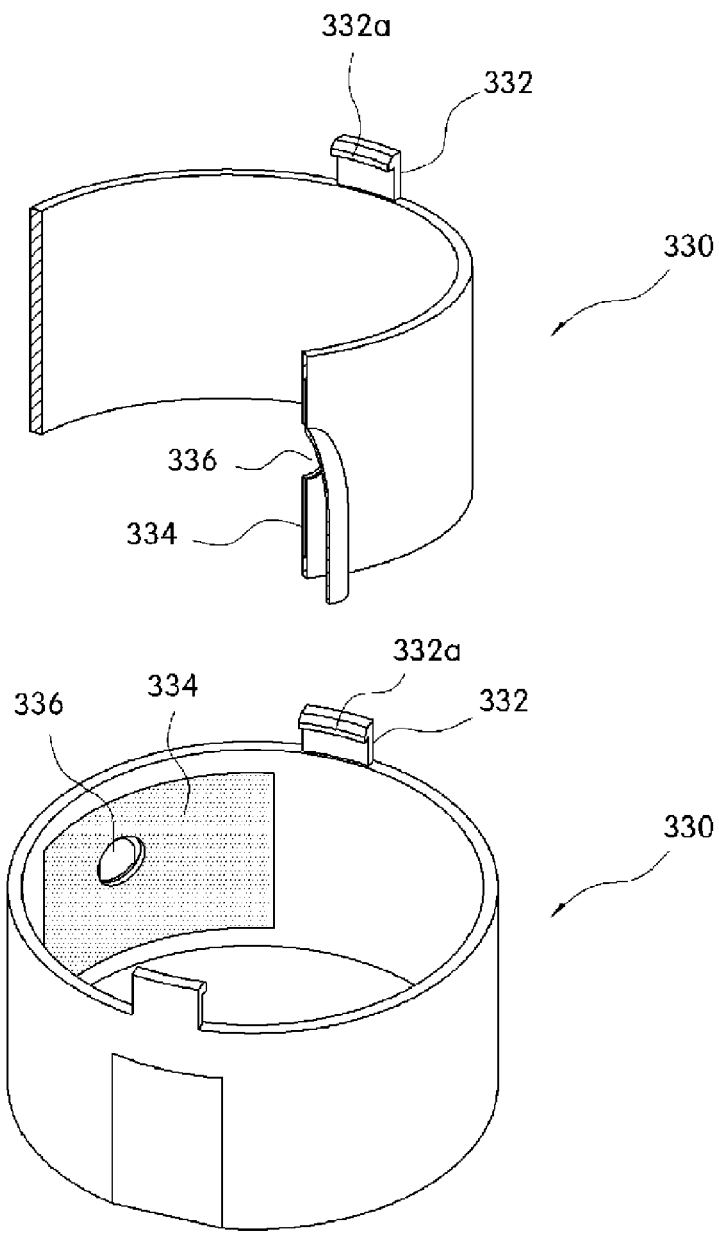
FIG. 14 is a partially cut-away and top perspective view illustrating an opening and closing part in FIG. 9.

As illustrated in FIG. 14, the opening and closing part 330 is engaged to the lower side of the body 310 and may allow to open and close the discharge hole 314 formed at a lower side of the body 310. This opening and closing part 330 may be formed in a circular hollow pillar shape the top and bottom of which are open and may include a ¬-shaped engaging part 332 which extents at a predetermined height from the top and a discharge opening 336 through which ingredients may move.

Here, the engaging part 332 may slide along a cut-away groove 316 which is formed cut-away with a predetermined depth on a side portion of the body 310 from the lower side to the upper side and may be engaged to the lower side of the body 310.

At this time, on the top of the cut-away groove 316, a slit groove 316b may be formed cut-away with a predetermined length, so a protrusion end 332a of the engaging part 332 may be engaged to the slit groove 316a. To this end, if the engaging part 332 is rotated in one direction, the protrusion end 332a of the engaging part will slide along the slit groove 316a, which makes the engaging part 332 rotate. To this end, when different kinds of ingredients are mixed with the aid of the mixing part 320 and in the inner space of the body 310, the opening and closing part 330 is rotated in one direction, and the protruding end 332a of the engaging part 332 will be moved to an end portion of the slit groove 316a. To this end, the discharge hole 314 formed at the body 310 and the discharge ort 336 formed at the opening and closing part 330 become communicated, so the cosmetic mixed in the inner space of the body 310 can be discharged to the outside through the discharge hole 314 and the discharge opening 336.

In a state where the protruding end 332a of the engaging part 332 positions at the other end of the slit groove 316a, since the discharge opening 336 and the discharge hole 314 are not communicating with each other, the ingredients stored in the inner space of the body 310 are prevented from being discharged to the outside through the discharge hole 314, so different kinds of ingredients can be mixed in the inner space of the body 310 with the aid of the rotations of the mixing part 320.

Meanwhile, the drawings show that the opening and closing part 330 may allow the cosmetics, wherein the mixing of ingredients has been finished, to be discharged to the outside since the discharge opening 336 and the discharge hole 314 can communicate with each other with the aid of rotations in the engaged structure of the engaging part 332 and the slit groove 316a, but it is not limited thereto. It is obvious that various methods, for exampoule, a slide type, a button type, etc. may be adapted, wherein the discharge route of the mixing-completed cosmetic can be sealed or opened.

In addition, it is preferred that a pad 334 having a predetermined area at a periphery of the discharge part 336 may be provided between the inner surface of the opening and closing part 330 and the outer surface of the body 310, so it can be possible to prevent the ingredients stored in the inner space of the body 310 from being discharged to the outside through the gap between the engaged portions when engaging the opening and closing part 330 and the body 310.

Figure 15A:
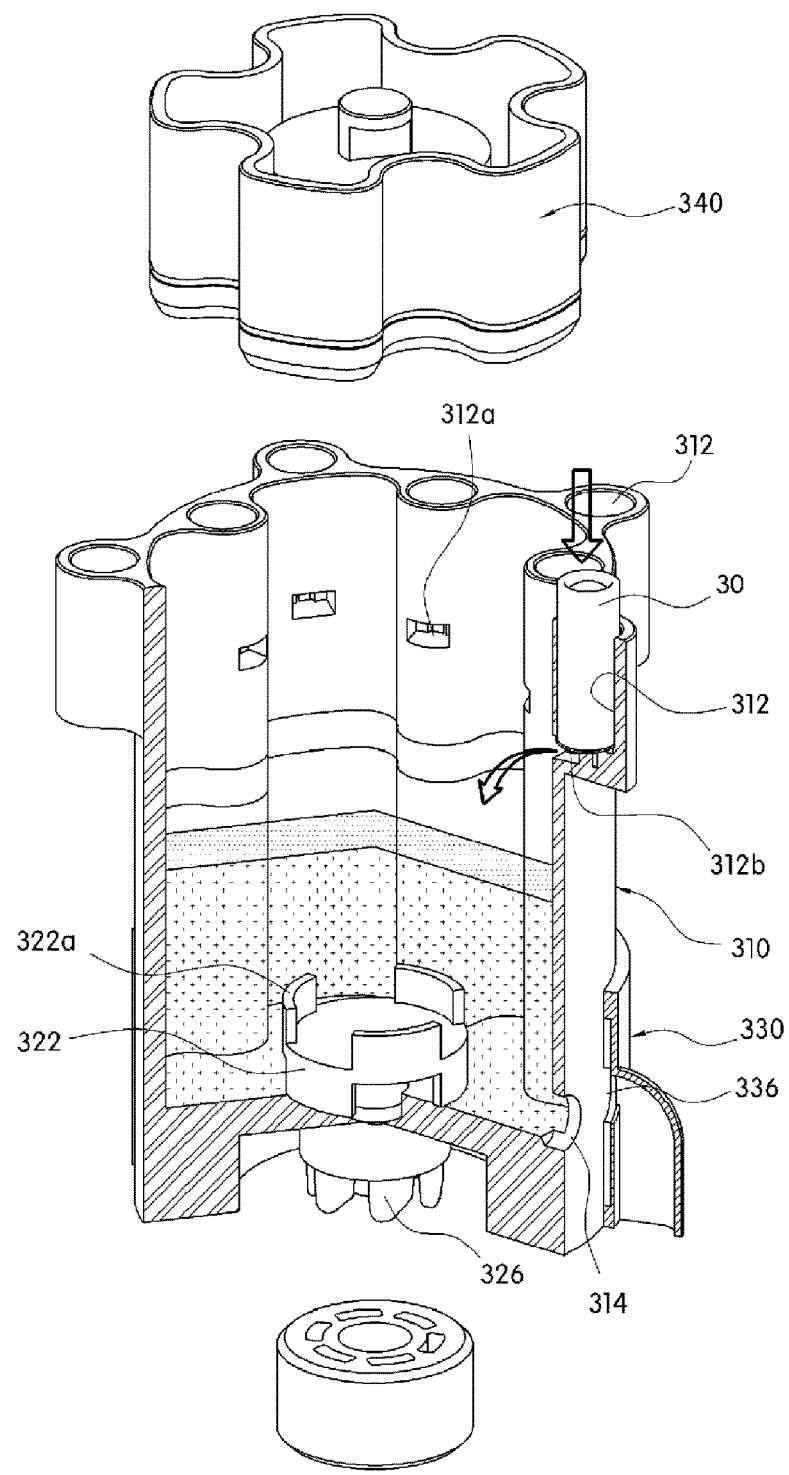
FIGS. 15A to 15C are flow charts for describing a procedure for mixing different kinds of raw ingredients by using a throwaway cosmetic mixing container according to the present invention.
Figure 15B:
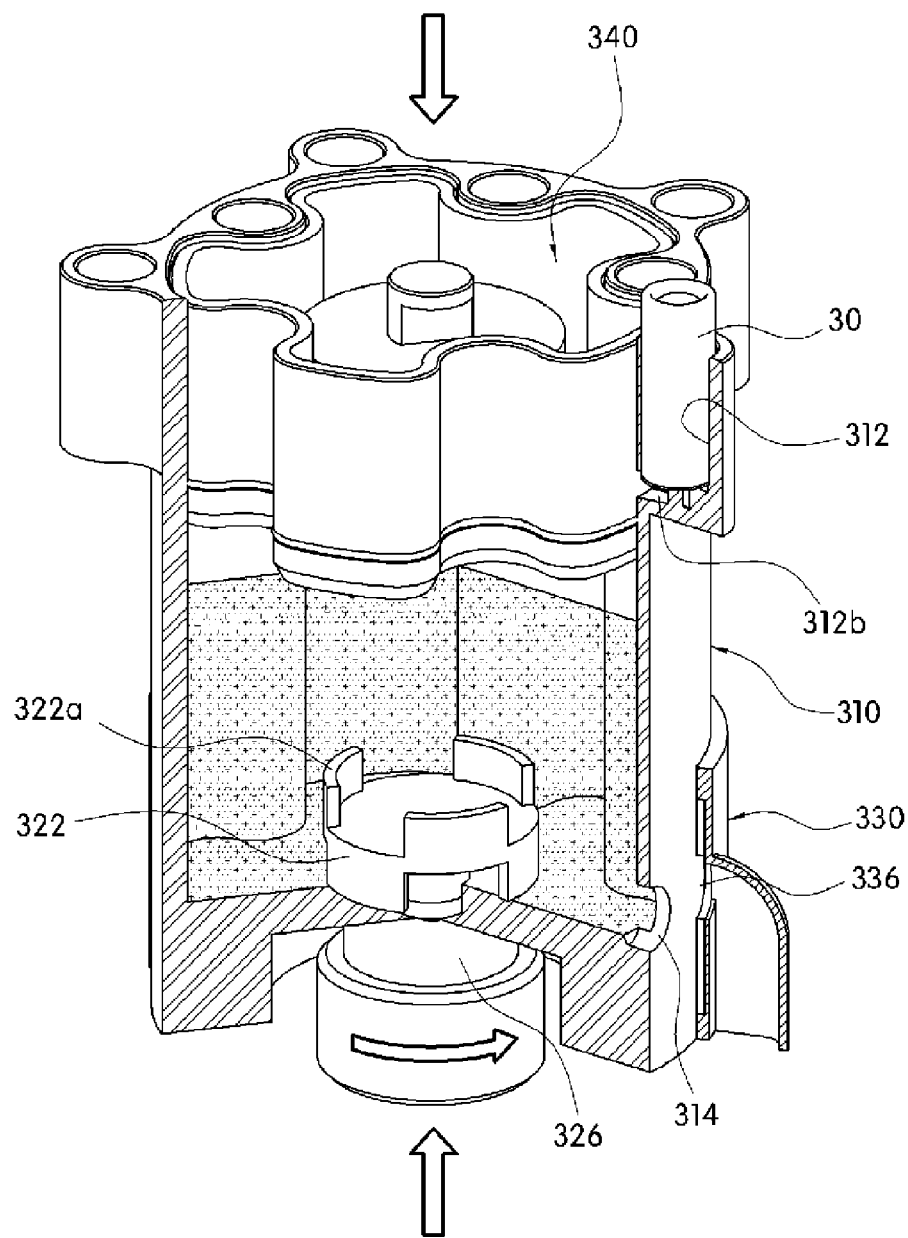
Figure 15C:
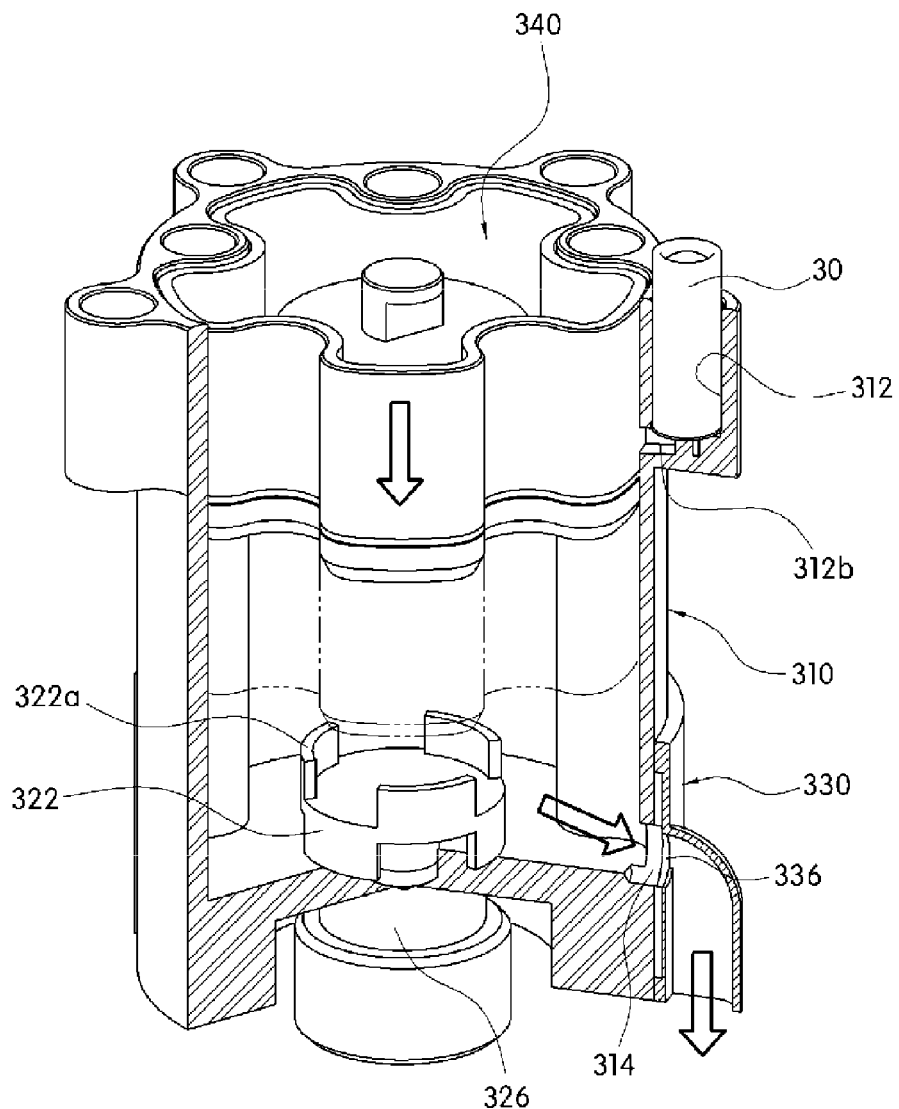

Referring to FIGS. 15A to 15C, the procedure for mixing different kinds of cosmetic ingredients using the throwaway cosmetic mixing container 300 according to the present invention will be described. For conveniences, the operation begins in a state where a base ingredient, which may be an ingredient of cosmetic, is stored by a predetermined amount in the inside of the body 310, and the ampoule 30 is filled with a sub-ingredient or a functional ingredient.

Referring to FIG. 15A, the base ingredient is filled by a predetermined amount in the inner space of the body 310, and the ampoule 30 filled with a sub-ingredient or a functional ingredient is fitted into the ampoule fitting part 312. Thereafter, the pressing part 340 is engaged to the top of the body 310, and external force is delivered to the top of the ampoule 30 fitted in the ampoule fitting part 312 in a state where the open top is sealed. In this state, the ampoule 30 may move downward by the external force, and the lower side will be cut away by the knife blade 312b provided on the bottom surface of the ampoule fitting part 312, and the sub-ingredient or the functional ingredient stored in the inside may be discharged from the ampoule 30 and may be inputted into the inner space of the body 310 through the discharge passage 312a formed on the bottom surface of the ampoule fitting part 312.

Thereafter, referring to FIG. 15B, external force may be supplied in such a way that the motor engaging part 326 coupled to the lower side of the body 310 is connected to a separate motor using a coupler thus rotating the rotation blade part 322. When the mixing of the base ingredient and sub-ingredient or functional ingredient stored in the inner space of the body 310 is completed with the aid of the rotations of the rotation blade part 322, the rotations of the rotation blade part 322 is stopped, and the opening and closing part 330 is rotated in one direction, so that the discharge opening 336 of the opening and closing part 330 and the discharge hole 314 of the body 310 can communicate with each other.

Finally, referring to FIG. 15C, the mixture in the inner pace is pushed by moving downward the pressing part 340 engaged to the top of the body 310, whereupon the mixing-completed cosmetic can be completely discharged to the outside through the discharge opening 336.

Here, the driving force which allows to press downward the ampoule 30 fitted in the ampoule fitting part 312 or press downward the pressing part 340 and the rotations of the rotation blade part 322 may be obtained the motor (not illustrated) provided at the instant cosmetic preparation device which equips with the mixing container 300.

As described above, according to the present invention, the customer can select in person a main ingredient and a sub-ingredient based on his desired or need, so it is possible to instantly manufacture a customized cosmetic that the customer wants to.

According to the present invention, the ampoule filled with a predetermined amount of ingredients is fitted into the ampoule fitting part provided in the body of the mixing container, and different kinds of ingredients can be inputted through the discharge passage into the inside of the body, which corresponds to an inner space of the body, thus manufacturing high quality cosmetics.

As the present invention may be embodied in several forms without departing from the spirit or essential characteristics thereof, it should also be understood that the above-described exampoules are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

What is claimed is:

1. An instant cosmetic preparation device, comprising:
   a housing;
   a finished product container transfer part disposed at an inside of the housing, the finished product container transfer part being configured to transfer a finished product container filled with a cosmetic mixture stored inside the housing to a sealing position;
   a sealing part disposed on a top of the finished product container transfer part in the inside the housing, the sealing part being configured to seal an open injection port of the finished product container;
   a control unit disposed at the inside the housing, the control unit being configured to control the operation of the sealing part,
   an upper transfer plate disposed on an upper surface of the finished product container transfer part and including a mounting groove with a predetermined depth, the upper transfer plate being configured to move forward and backward; and
   a lower transfer pate disposed on a lower surface of the finished product container transfer part, the lower transfer pate being configured to move leftward and rightward.

2. The apparatus of claim 1, further comprising:
   a panel operation part which is engaged at an outer side of the housing and is configured to select at least one or more of a base ingredient containing a specific natural substance and a sub-ingredient containing a specific functional substance and/or select a sealing method;
   a mixing container delivery part which is disposed on the top of the finished product container transfer part in the inside of the housing, wherein a plurality of base ingredient storing containers filled by a predetermined amount and with the base ingredient are stacked, the mixing container delivery part being configured to deliver, if necessary, the base ingredient storing container to a mixing position of the base ingredient and the sub-ingredient;
   a sub-ingredient delivery part which is disposed on the top of the finished product container transfer part in the inside of the housing, wherein a plurality of sub-ingredient storing containers filled by a predetermined amount and with the sub-ingredient are stacked, the sub-ingredient delivery part being configured to input at least one or more of the sub-ingredient container into a holder which positions on the top of the base-ingredient storing container which is delivered to the mixing container delivery part, if necessary, in accordance with a selection on the panel operation part;
   an agitating part which is disposed on the top of the finished product container transfer part in the inside of the housing, the agitating part being configured to press the sub-ingredient, open the opening of the sub-ingredient container, and input the sub-ingredient into the base ingredient storing container, thus mixing the base ingredients and the sub-ingredient;
a rotation plate which is disposed on the top of the finished product container transfer part in the inside of the housing, the rotation plate being configured to move the position of the base ingredient storing container delivered from the mixing container delivery part to a lower side of the sub-ingredient delivery part or the agitating part in accordance with a control of the control unit; and
an injection part which is disposed on the top of the finished product container transfer part in the inside of the housing, the injection part being configured to open a discharge opening of a lower side of the base ingredient storing container when the operation of the agitating part is completed, press the top of the finished product container and inject the mixture mixed with the base ingredient and the sub-ingredient into the finished product container through the discharge opening.

3. The apparatus of claim 2, wherein the base ingredient storing container and the sub-ingredient storing container are throwaway containers which may be discarded after use.

4. The apparatus of claim 2, wherein the mixing container delivery part includes a first vertical tray on which a plurality of mixing container accommodation parts arranged in multiple rows are mounted, the first vertical tray being configured to move leftward and rightward in accordance with a control of the control unit.

5. The apparatus of claim 2, wherein the sub-ingredient delivery part includes:
a second vertical plate disposed on the top of the finished product container transfer part, the second vertical plate being configured to move leftward and rightward in accordance with a control of the control unit;
a first transfer body coupled to the second vertical plate, the first transfer body being configured to move upward and downward in accordance with a control of the control unit; and
a sub-ingredient accommodation part coupled to the first transfer body, wherein a plurality of sub-ingredients are stacked in an inside of the sub-ingredient accommodation part.

6. The apparatus of claim 2, wherein the injection part includes:
a second transfer body coupled to the second vertical plate, the second transfer body being configured to linearly move in upward and downward in accordance with a control of the control unit; and
a pressing plate provided at a lower side of the second transfer body.

7. The apparatus of claim 2, wherein the rotation plate includes:
a circular plate body; and
a plurality of container engaging parts formed along an outer circumferential surface of the circular plate body, wherein
a central shaft is coupled to the rotation plate to rotate the circular plate body.

8. The apparatus of claim 2, wherein the mixing container include:
a cylindrical body;
an agitating blade which is installed at an underside portion of the cylindrical body and is configured to rotate in one direction; and
at least one or more of a discharge opening which is formed on the underside portion of the cylindrical body.

9. The apparatus of claim 1, wherein the sealing part includes a first finishing part and/or a second finishing part, the first sealing part including:
an inner cap delivery part disposed on the top of the finished product container transfer part, wherein a plurality of inner caps are stacked in the inner cap delivery part, the inner cap delivery part being configured to temporarily fix each of the inner caps at the open injection port of the finished product container in accordance with a control of the control unit;
an inner cap engaging part disposed on the top of the finished product container transfer part;
a rod installed at the inner cap engaging part, the rod configured to move upward and downward; and
a cap pressing plate provided at a lower side of the rod, the cap pressing plate configured to press the temporarily fixed inner cap, wherein the second finishing part includes a pair of heat plates to seal the open injection port of the finished product container.

10. An instant cosmetic preparation device, comprising:
a housing which includes at least one or more of a finished product container input port;
a panel operation part which is engaged at an outer side of the housing and is configured to select a base ingredient containing a specific natural substance and at least one or more of a sub-ingredient containing a specific functional substance and/or a sealing method;
a finished product container transfer part which positions in the inside of the housing and is configured to transfer the finished product container placed on the finished product container input port to a lower end of the position where the base ingredient and the sub-ingredient are agitated;
a mixing container delivery part which positions on the top of the finished product container transfer part and in the inside of the housing, wherein a plurality of base ingredient storing containers filled by a predetermined amount with the base ingredient are stacked, the mixing container delivery part being configured to deliver the base ingredient storing container to the mixing position of the base ingredient and the sub-ingredient;
a sub-ingredient delivery part which positions on the top of the finished product container transfer part and in the inside of the housing, wherein a plurality of sub-ingredient storing containers filled by a predetermined amount with the sub-ingredient are stacked, the sub-ingredient delivery part being configured to input at least one or more of the sub-ingredient container to a holder which positions on the top of the base ingredient storing container delivered to the mixing container delivery part, if necessary, in accordance with a selection on the panel operation part;
an agitating part which is disposed on the top of the finished product container transfer part and in the inside of the housing, the agitating part being configured to press the sub-ingredient, open the opening of the sub-ingredient container, and input the sub-ingredient into the base ingredient storing container, thus mixing the base ingredients and the sub-ingredient;
a transfer plate which positioned on the top of the finished product container transfer part and in the inside of the housing and is configured to move the position of the base ingredient storing container delivered from the mixing container delivery part to the lower end of the sub-ingredient delivery part or the agitating part;
an injection part which is disposed on the top of the finished product container transfer part and in the inside of the housing, the injection part being configured to open a discharge opening of a lower side of the base ingredient storing container when the operation of the agitating part is completed, press the top of the finished product container and inject the mixture mixed with the base ingredient and the sub-ingredient into the finished product container through the discharge opening; and a control unit which positions in the inside of the housing and is configured to selectively control the operations of the finished product container transfer part, the mixing container delivery part, the sub-ingredient delivery part, the agitating part, the transfer plate and the injection part.

11. The apparatus of claim 10, further comprising:

a sealing part which positions in the inside of the housing and is configured to seal an open injection port of the finished product container.

12. A throwaway cosmetic mixing container, comprising:

a body having at least one or more of a discharge hole and an inner space the top of which is open;

a plurality of insertion holes which are disposed at one side of the body;

a mixing means which is arranged in the inner space and is configured to mix different kinds of ingredients stored in the inner space; and an opening and closing means which equips with a discharge opening communicating with the discharge hole so as to discharge to the outside the ingredients mixed by the mixing means and is coupled to a lower side of the body.

13. The container of claim 12, wherein a pressing part configured to press downward the ingredient stored in the inner space is engaged detachable to an open top of the body.

14. The container of claim 12, wherein the mixing means includes a rotation blade part formed of a plurality of blades and engaged rotatable to a bottom surface of the body; and a motor engaging part which is engaged with the rotation blade part through an engaging shaft and is disposed at the lower side of the body and is engaged with an external motor.

* * * * *